US012619799B2

(12) United States Patent
Kenyon

(10) Patent No.: US 12,619,799 B2
(45) Date of Patent: May 5, 2026

(54) SYSTEM AND METHODS FOR SIMULATION OF MEDICAL DEVICES

(71) Applicant: Regeneron Pharmaceuticals, Inc., Tarrytown, NY (US)

(72) Inventor: Ross Kenyon, Saratoga Springs, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 1071 days.

(21) Appl. No.: 17/657,500

(22) Filed: Mar. 31, 2022

(65) Prior Publication Data

US 2022/0318455 A1 Oct. 6, 2022

Related U.S. Application Data

(60) Provisional application No. 63/169,601, filed on Apr. 1, 2021.

(51) Int. Cl.
| | |
|---|---|
| *G06F 30/20* | (2020.01) |
| *A61M 5/20* | (2006.01) |
| *G01N 3/08* | (2006.01) |
| G06F 111/10 | (2020.01) |

(52) U.S. Cl.
CPC ........... *G06F 30/20* (2020.01); *A61M 5/2033* (2013.01); *G01N 3/08* (2013.01); *G01N 2203/0071* (2013.01); *G01N 2203/0075* (2013.01); *G06F 2111/10* (2020.01)

(58) Field of Classification Search
CPC ....... G06F 30/20; G06F 2111/10; G01N 3/08; G01N 2203/0071; G01N 2203/0075

USPC .............................................. 703/6
See application file for complete search history.

(56) References Cited

U.S. PATENT DOCUMENTS

| | | | |
|---|---|---|---|
| 2002/0157478 | A1 | 10/2002 | Seale |
| 2002/0178832 | A1 | 12/2002 | Sarabi et al. |
| 2007/0261500 | A1 | 11/2007 | Harrell, Jr. |
| 2018/0164199 | A1 | 6/2018 | Miyajima |
| 2019/0050375 | A1 | 2/2019 | Fitzgibbon et al. |
| 2020/0093992 | A1 | 3/2020 | Gibson et al. |

FOREIGN PATENT DOCUMENTS

| | | |
|---|---|---|
| CN | 104568602 A | 4/2015 |
| RU | 1788460 A1 | 1/1993 |
| RU | 2400727 C1 | 9/2010 |
| SU | 922575 A1 | 4/1982 |
| SU | 1033923 A2 | 8/1983 |

(Continued)

OTHER PUBLICATIONS

Jeff Ellis, "Long-term. Polymer Properties—Don't Be Creepy, Just Relax the Stress Away", Oct. 22, 2020, XP055941062, Retrieved from the Internet: URL:https://ewi.org/polymer-creep-and-stress-relaxation-in-medtech-devices/, pp. 1-5.

(Continued)

*Primary Examiner* — Brian S Cook
(74) *Attorney, Agent, or Firm* — Bookoff McAndrews, PLLC

(57) ABSTRACT

Disclosed herein are devices and methods for generating and/or verifying a predictive temperature stress and time creep modulus, approving or rejecting a medical device, verifying a medical device design using a linear device model, and generating coefficients using thermal analysis.

19 Claims, 21 Drawing Sheets

(56) References Cited

FOREIGN PATENT DOCUMENTS

| | | | |
|---|---|---|---|
| SU | 1060976 | A1 | 12/1983 |
| WO | 2018204779 | A1 | 11/2018 |

OTHER PUBLICATIONS

Ildar, Karimov. "Lecture 18. Creep of materials", <https://soprotmat. ru/polzuch.htm>, Accessed Apr. 30, 2024 (16 pages).
International Search Report and Written Opinion mailed Oct. 19, 2022 in International Application No. PCT/US2022/022842 (26 pages).
Thomas Thueer et al., "Development of an advanced injection time model for an autoinjector", Medical Devices: Evidence and Research, Dec. 31, 2018, vol. 11, pp. 215-224.
Jonathan Wilkins et al., "Mathematical Modeling for Faster Autoinjector Design", Innovations in Pharmaceutical Technology, Issue 42, Jul. 31, 2012, pp. 42-45.

340

320

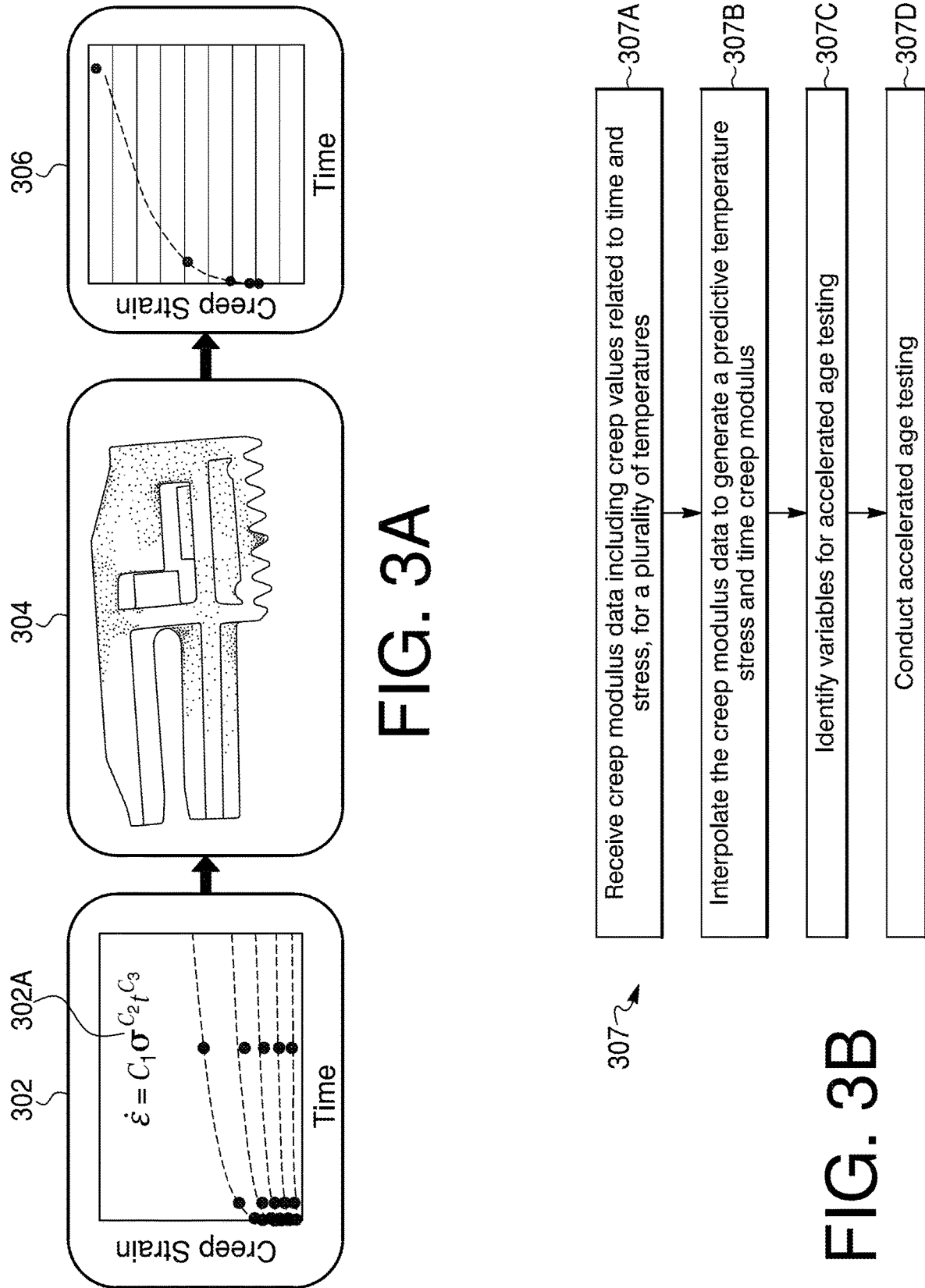

302
302A $$\dot{\varepsilon} = C_1 \sigma^{C_2} t^{C_3}$$

Creep Strain

Time

304

306

Creep Strain

Time

307A Receive creep modulus data including creep values related to time and stress, for a plurality of temperatures 307B Interpolate the creep modulus data to generate a predictive temperature stress and time creep modulus 307C Identify variables for accelerated age testing 307D Conduct accelerated age testing

SYSTEM AND METHODS FOR SIMULATION OF MEDICAL DEVICES

CROSS-REFERENCE TO RELATED APPLICATIONS

This application claims priority to U.S. Provisional Application No. 63/169,601, filed Apr. 1, 2021, the entire disclosure of which is hereby incorporated herein by reference in its entirety.

FIELD OF DISCLOSURE

Aspects of the present disclosure relate to designing and testing devices, e.g., medical devices such as auto-injectors, based on simulating device properties and/or age testing. More specifically, embodiments of the present disclosure relate to auto-injectors and methods for developing auto-injectors and related components that meet quality and use criteria.

INTRODUCTION

Various available medical devices, such as auto-injectors, include a plurality of components. The medical devices as a whole and/or one or more of the plurality of components are often required to meet quality or use criteria so the medical devices can operate in an acceptable manner for duration of their respective lifespans. Deviation from the quality or use criteria may result in sub-optimal performance or failure of the medical devices. However, testing multiple iterations of a medical device design and updating the device and/or its components to meet the quality or use criteria may not be possible due to time and/or cost constraints. Accordingly, an efficient way to determine whether a medical device with a given design meets one or more quality or use criteria is required.

SUMMARY

Disclosed herein are methods and systems to analyze medical devices and/or designs. In one embodiment of the present disclosure a method for determining accelerated testing parameters for a medical device includes receiving raw creep modulus data relating creep strains to durations of stress and amounts of stress, as a factor of a range of temperatures; generating a predictive modulus based on the raw creep modulus data; and generating, using the predictive modulus, one or more of an accelerated testing time, an accelerated stress, or an accelerated temperature.

The accelerated testing time is generated based on a reference creep strain, a reference stress, and the accelerated temperature. The method includes generating an accelerated testing creep strain based on accelerated testing of the medical device, the accelerated testing conducted based on the accelerated temperature, the accelerated testing time, and the accelerated stress; and outputting one of a medical device approval indication or a medical device rejection indication based on comparing the accelerated testing creep strain and the reference creep strain. The approval indication approves the medical device and the rejection indication rejects the medical device. The method further includes generating an accelerated testing creep strain based on accelerated testing of the medical device, the accelerated testing conducted based on the accelerated temperature, the accelerated testing time, and the accelerated stress; and outputting one of a predictive modulus approval indication or a predictive modulus rejection indication, based on comparing the accelerated testing creep strain and the reference creep strain. The medical device is manufactured based on a medical device design corresponding to another medical device, wherein the raw creep modulus data is based on the other medical device. The predictive modulus is generated based on a three-dimensional (3D) interpolation of the raw creep strain data. The raw creep strain data is generated based on one of simulated strain or experienced strain.

In another embodiment of the present disclosure a method for method for validating a predictive modulus for a medical device includes receiving raw creep strain data relating creep strain values to durations of stress and amounts of stress, as a factor of a range of temperatures; generating a predictive modulus, the predictive modulus being configured to output an accelerated temperature, an accelerated time, and an accelerated stress based on a reference creep strain; receiving the accelerated temperature, the accelerated time, and the accelerated stress based on the reference creep strain; receiving an accelerated testing creep strain for the medical device based on accelerated testing conducted based on the accelerated temperature, the accelerated time, and the accelerated stress; and outputting one of an approval indication or a rejection indication based on comparing the accelerated testing creep strain and the reference creep strain.

According to the method, the predictive modulus is generated based on a three-dimensional (3D) interpolation of the raw creep strain data. A first creep strain for a first duration of time, a first amount of stress, and a first temperature is different than a second creep strain for the first duration of time, the first amount of stress, and a second temperature. The reference creep strain corresponds to a reference temperature, a reference time, and a reference stress. The reference temperature is an ambient temperature, the reference time is an anticipated shelf life for the medical device, and the reference stress is an anticipated amount of stress. The approval indication approves the predictive modulus and the rejection indication rejects the predictive modulus.

In another embodiment of the present disclosure a method for validating a medical device design includes receiving a plurality of medical device relationships based on the medical device design, wherein the plurality of medical device relationships correspond to voltage, current, resistance, torque, speed, and force relationships for the medical device design and includes a plurality of coefficients; generating a linear device model based on the plurality of medical device relationships; receiving simulated coefficient values for each of the plurality of coefficients from a distribution function, for the plurality of medical device relationships; generating simulated output distributions for a voltage, a current, a resistance, a torque, a speed, or a force, based on the simulated coefficients and the linear device model; comparing the simulated output distributions to a threshold output requirement; and outputting one of an approval indication or a rejection indication based on comparing the simulated output distributions to the threshold output requirement.

According to the method, the distribution function is a normal distribution function or a mixture of normal distribution functions. Comparing the simulated output distributions to the threshold output requirement includes comparing a maximum distribution value to a maximum threshold output requirement, comparing a minimum distribution value to a minimum threshold output value, or comparing a peak distribution value to a peak threshold output value. The simulated output distributions are based on at least ten thousand simulations performed in less than one hour. The plurality of medical device relationships are based on a substance viscosity, wherein the substance viscosity is calculated based on a substance temperature behavior determined based on a thermal analysis. A coefficient of the plurality of coefficients is generated based on a fluid path restriction analysis, the fluid path restriction analysis outputting a force exerted as a factor of determined viscosity and determined speed.

BRIEF DESCRIPTION OF THE DRAWINGS

The accompanying drawings, which are incorporated into and constitute a part of this specification, illustrate various exemplary embodiments and, together with the description, serve to explain principles of the disclosed embodiments. The drawings show different aspects of the present disclosure and, where appropriate, reference numerals illustrating like structures, components, materials, and/or elements in different figures are labeled similarly. It is understood that various combinations of the structures, components, and/or elements in various embodiments, other than those specifically shown, are contemplated and are within the scope of the present disclosure.

There are many embodiments described and illustrated herein. The described devices and methods are neither limited to any single aspect nor embodiment thereof, nor to any combinations and/or permutations of such aspects and/or embodiments. Moreover, each of the aspects of the described inventions, and/or embodiments thereof, may be employed alone or in combination with one or more of the other aspects of the described inventions and/or embodiments thereof. For the sake of brevity, certain permutations and combinations are not discussed and/or illustrated separately herein.

FIG. 3A includes illustrations to identify a creep strain profile, according to an example of the disclosure.

FIG. 3B includes a flowchart for generating creep strain relationships, according to an example of the disclosure.

4

Figure 10:

FIG. 10 shows a thermal analysis, according to an example of the disclosure.

Figure 11:
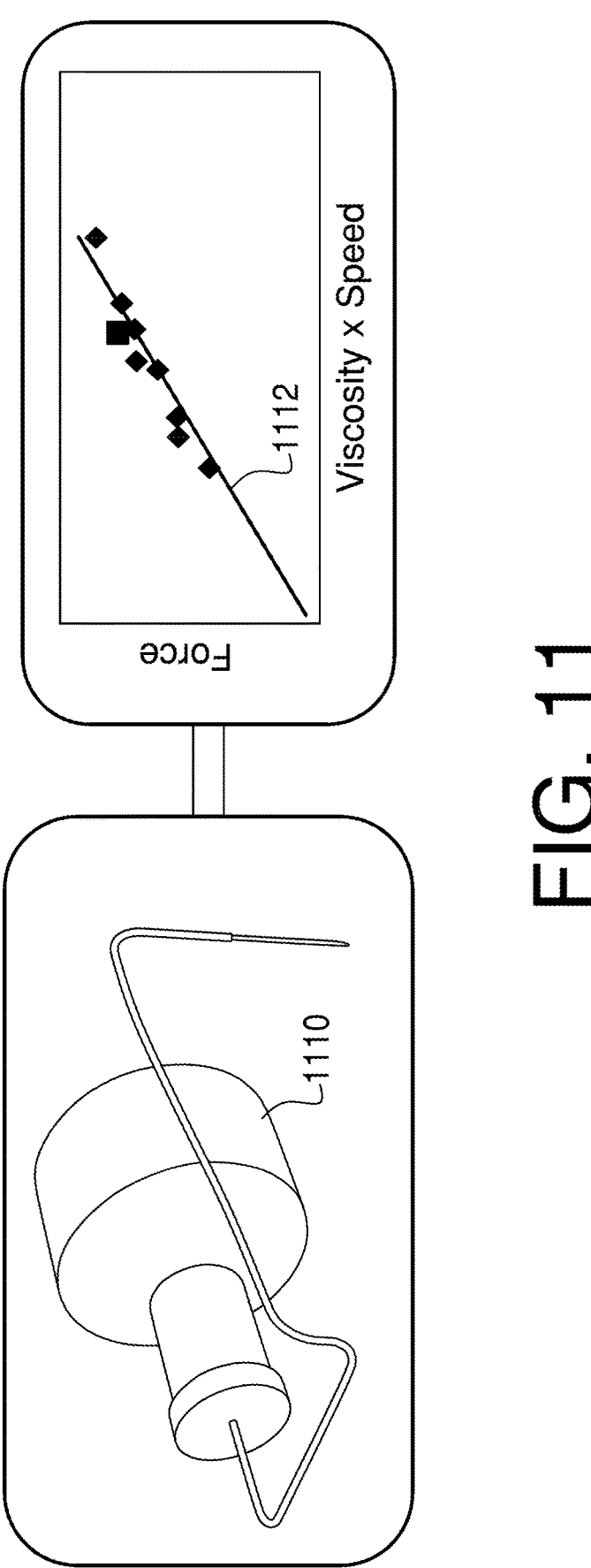

FIG. 11 shows a fluid path restriction analysis, according to an example of the disclosure.

Figure 12:
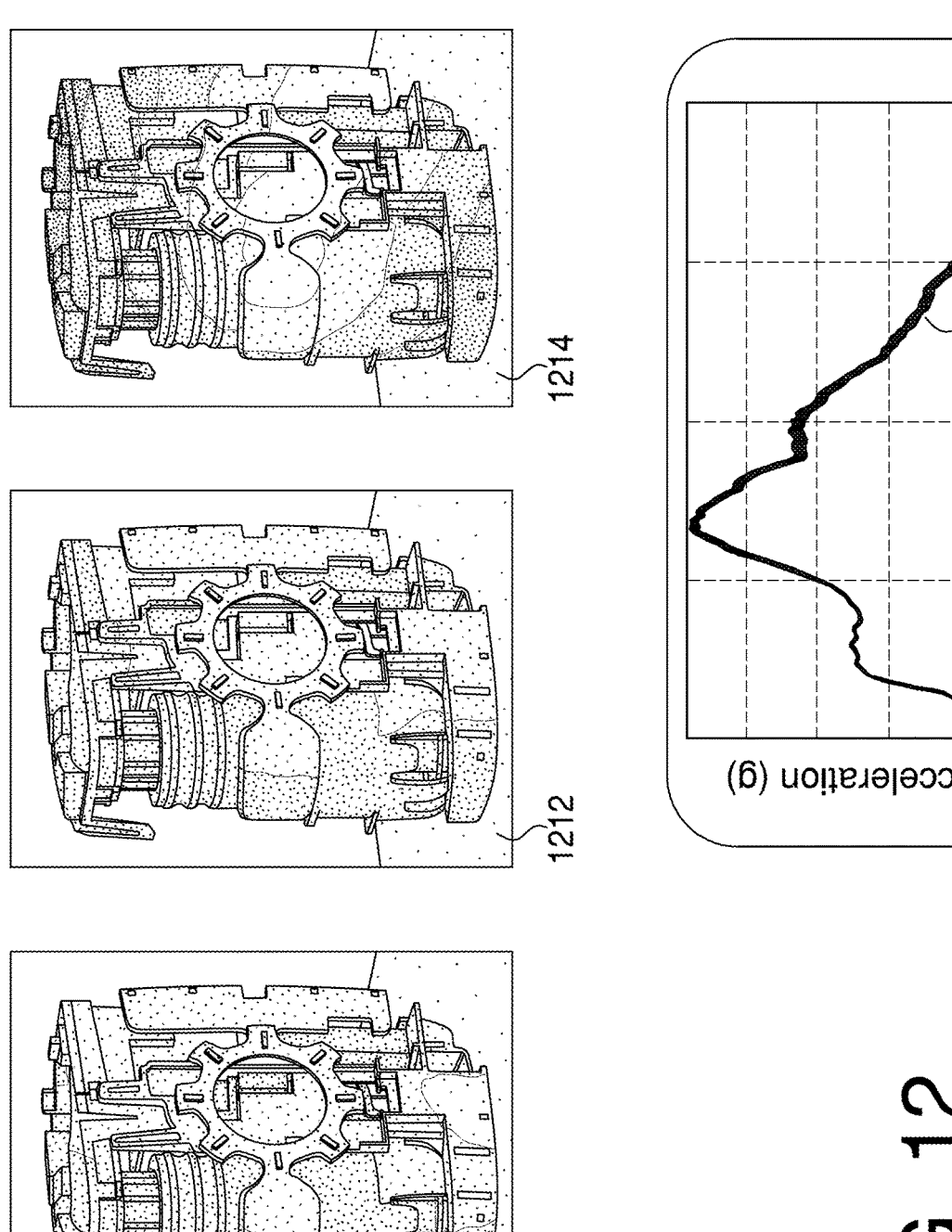

FIG. 12 shows drop testing analysis results, according to an example of the disclosure.

Figures 13A, 13B, 13C:
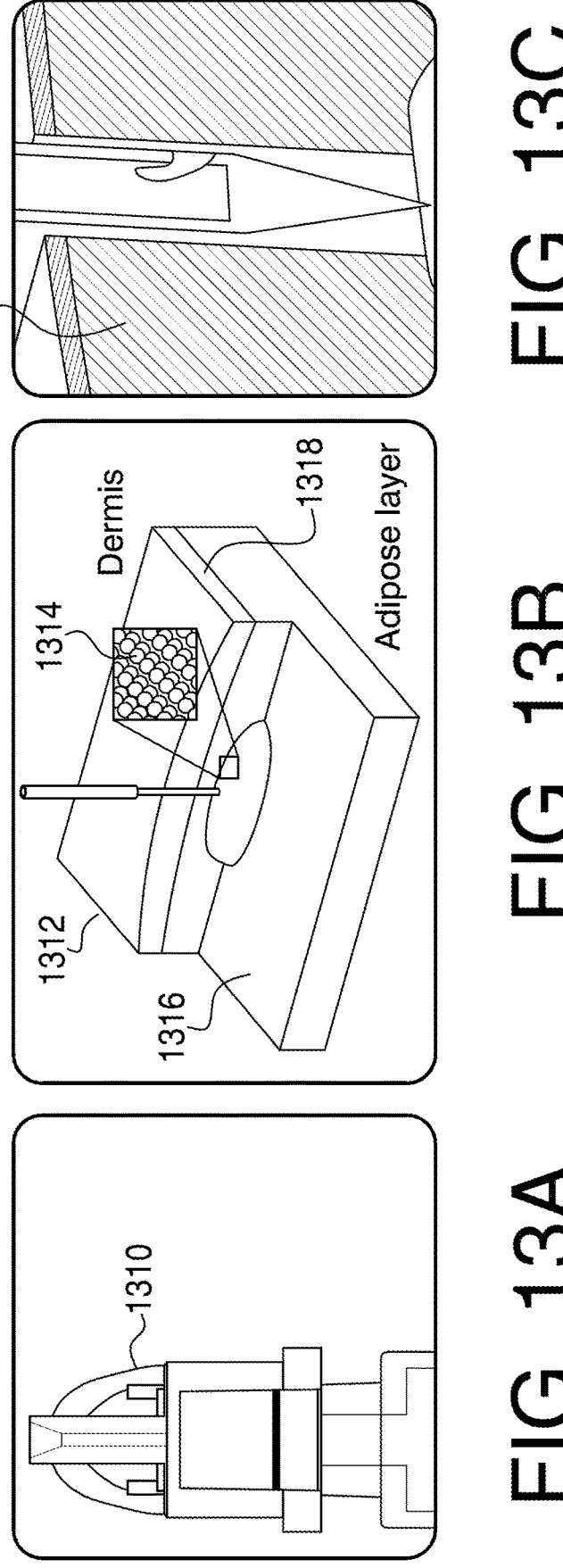

FIG. 13A shows a leakage assessment, according to an example of the disclosure.

FIG. 13B shows a physiological model, according to an example of the disclosure.

FIG. 13C shows needle coring, according to an example of the disclosure.

Figure 14:
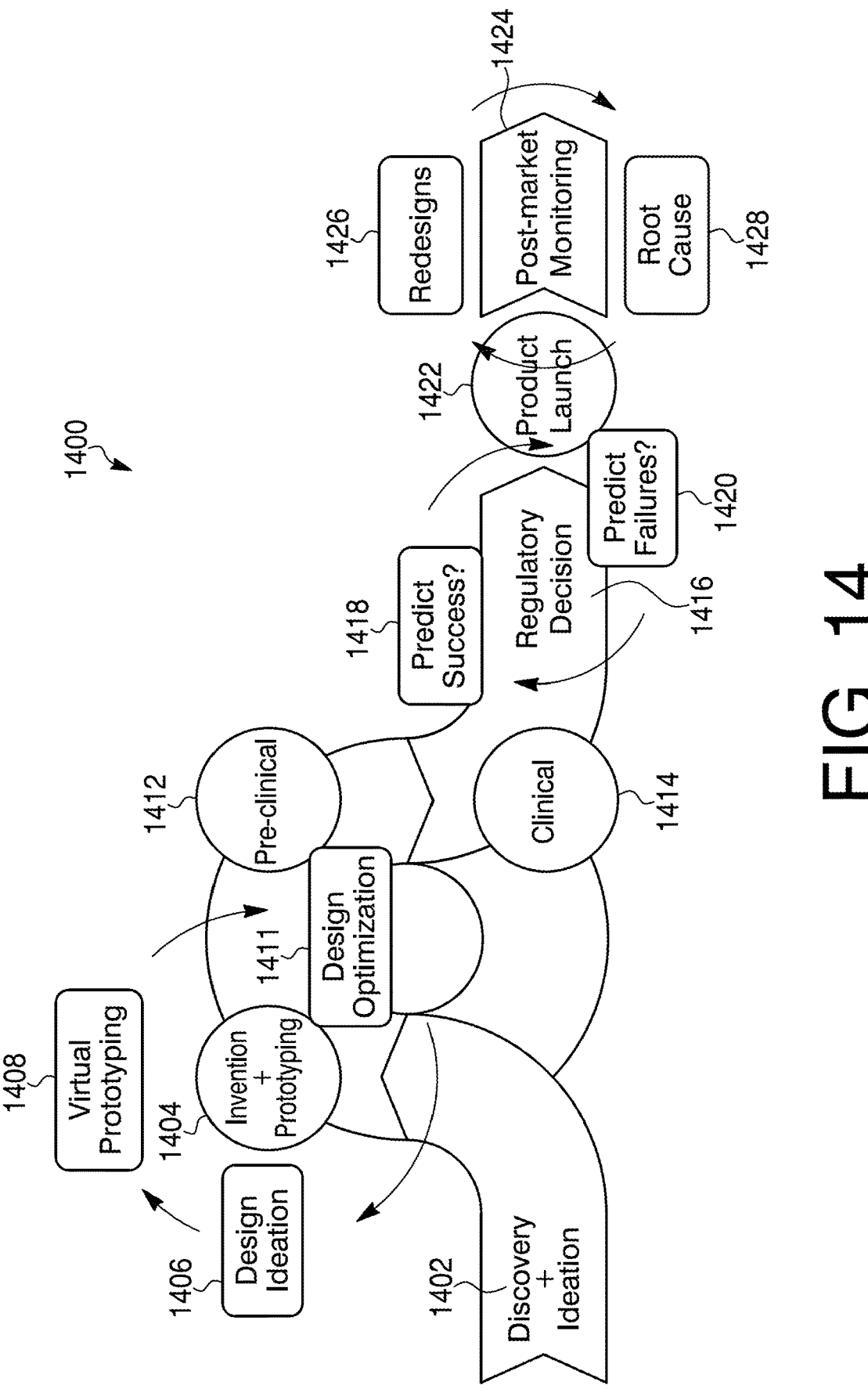

FIG. 14 shows a product life cycle, according to an example of the disclosure.

An appendix of accompanying figures illustrating various exemplary embodiments is included together with the description and drawings described above, which is incorporated into and constitutes a part of this specification.

There are many embodiments described and illustrated herein. The present disclosure is neither limited to any single aspect nor embodiment thereof, nor to any combinations and/or permutations of such aspects and/or embodiments. Each of the aspects of the present disclosure, and/or embodiments thereof, may be employed alone or in combination with one or more of the other aspects of the present disclosure and/or embodiments thereof. For the sake of brevity, many of those combinations and permutations are not discussed separately herein.

Notably, for simplicity and clarity of illustration, certain aspects of the figures depict the general structure and/or manner of construction of the various embodiments. Descriptions and details of well-known features and techniques may be omitted to avoid unnecessarily obscuring other features. Elements in the figures are not necessarily drawn to scale; the dimensions of some features may be exaggerated relative to other elements to improve understanding of the example embodiments. For example, one of ordinary skill in the art appreciates that the cross-sectional views are not drawn to scale and should not be viewed as representing proportional relationships between different components. The cross-sectional views are provided to help illustrate the various components of the depicted assembly, and to show their relative positioning to one another.

DETAILED DESCRIPTION

Reference will now be made in detail to examples of the present disclosure, which are illustrated in the accompanying drawings. Wherever possible, the same reference numbers will be used throughout the drawings to refer to the same or like parts. Embodiments of the present disclosure may be used with any type of fluid-containing products, such as liquid drug substances, liquid placebos, or other liquids that may be dispensed in a dose form. In the discussion that follows, terms "about," "approximately," "substantially," and the like, when used in describing a numerical value, denote a variation of +/−10% of that value, unless specified otherwise.

As used herein, the terms "comprises," "comprising," "includes," "including," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." Notably, an embodiment or implementation described herein as an "example" or "exemplary" is not to be construed as preferred or advantageous, for example, over other embodiments or implementations; rather, it is intended reflect or indicate the embodiment(s) is/are one "example," rather than "ideal."

As used herein, the terms "distal" and "distally" refer to a location (or portion of a device) relatively closer to, or in the direction of, a patient delivery site, and the terms "proximal" and "proximally" refer to a location (or portion of a device) relatively closer to, or in the direction of, a user end opposite a distal location/portion of a device. In addition, the terms "first," "second," and the like, herein do not denote any order, quantity, or importance, but rather are used to distinguish an element, a structure, a step or a process from another. Moreover, the terms "a" and "an" herein do not denote a limitation of quantity, but rather denote the presence of one or more of the referenced items.

As described above, existing auto-injectors include a plurality of components. An auto-injector as a whole and/or each of the plurality of components of an auto-injector may need to meet quality or use criteria to ensure usability of the auto-injector. Determining whether an auto-injector and/or its components meets one or more quality or use criteria can be done by testing a physical auto-injector and/or its physical components. However, such testing using a physical auto-injector may be cost and time prohibitive as iterative improvements to physical versions of an auto-injector may require manufacturing a new auto-injector for each iteration. Alternatively, determining whether an auto-injector and/or its components meets one or more quality or use criteria can be done by using accelerated testing chambers and/or generating simulations. However, existing techniques for accelerated testing do not account for parameters such as creep. Additionally, existing techniques for generating simulations are often resource intensive and time consuming.

Accordingly, the present disclosure is directed to various embodiments of simulation-based testing of medical devices (e.g., auto-injectors), which may be a complete device or a component of a device. Specifically, according to certain embodiments, creep modulus data may be received and/or generated for a given device, component, and/or material. The raw creep modulus data may include raw data including creep strains for a given device or component as a function of temperature, stress, and duration of stress. The creep strains may be expressed as strain values and/or relationships between creep strain and one or more of temperature, stress, and duration of stress. The raw creep strain data may be based on, for example, observed (e.g., using one or more sensors) or simulated creep strain experienced by a device or component at given temperatures and for given stresses over durations of time. The arrangement of components within an auto-injector, for example, may result in a constant stress or varying stresses being applied over time. For example, a spring within the auto-injector may be compressed and may apply a stress onto various components of the auto-injector. According to an implementation, raw creep strain data may be used to generate the relationships between creep strains and temperature, stress, and/or duration of stress.

The creep strain for the same duration of stress and same amount of stress may be different for different temperatures. For example, different creep strain relationships may be identified for each of a first, second, and third temperature and each based on different durations of stress and amounts of stress. Based on the plurality of creep strain relationships, interpolation (e.g., three-dimensional (3D)) may be used to generate a predictive temperature stress and time creep modulus (e.g., a predictive modulus). The predictive temperature stress and time creep modulus may be used to output creep strains as a function of stress and time for a plurality of arbitrary temperatures. The predictive temperature stress and time creep modulus may be used to determine variables (e.g., temperature, stress amount, stress duration) for an accelerated aging test. For example, the predictive temperature stress and time creep modulus for a given device or component may identify creep strain values for a given duration of time (e.g., 2 years) at a given temperature with a given amount of stress for the given device or component. The given amount of stress may correspond to an actual or theoretical amount of stress experienced by the given device or component.

The predictive temperature stress and time creep modulus may be used to identify variables (e.g., time, temperature, stress) that can be used in an accelerated test to observe an expected or experienced creep strain. The variables may be determined based on a selected creep strain value and/or one or more of a temperature, time, and/or stress. Accordingly, the accelerated test may be conducted using variables (e.g., an amount of time, a temperature, and an amount of stress) identified based on the predictive temperature stress and time creep modulus. The accelerated test may be used to determine a creep strain at the end of the accelerated test, and to compare the creep strain to an expected creep strain (e.g., the creep strain used to select the amount of time, temperature, and amount of stress for the accelerated test).

For example, a predictive temperature stress and time creep modulus may be generated based on interpolating raw creep modulus data for a given component. The predictive temperature stress and time creep modulus may be used to identify an accelerated duration of time and a testing stress amount to generate a given creep strain at an accelerated testing temperature (e.g., a higher than ambient temperature) that can be used for accelerated testing. The accelerated duration of time may be shorter than the duration of time that the component experiences the given creep strain, for example, at an ambient temperature.

An accelerated test of the component may be conducted using an aging chamber at the accelerated testing temperature for the identified duration of time, while the component experiences the testing stress amount. The aging chamber may be any applicable chamber that enables accelerated aging testing by artificially manipulating a property (e.g., temperature). At the end of the accelerated test for the accelerated duration of time, the creep strain for the component may be measured and compared to the given creep strain. The comparison may be used to verify the predictive temperature stress and time creep modulus and/or to determine if the component's observed creep strain at the end of the test is within a threshold range of the given (e.g., expected) creep strain.

As applied herein, "creep" or "creep strain" is a material property that refers to a tendency of a solid material to move (e.g., slowly) or deform (e.g., permanently) under the influence of persistent mechanical stresses. Creep strain may occur as a result of long-term exposure to stress that is otherwise below the yield strength of the material. The severity of creep strain in a given material may increase as a factor of heat and/or time. For example, creep strain may increase more when exposed to stress at a higher temperature (e.g., the effect of the temperature may be greatest near a given material's melting point) when compared to the same stress at a lower temperature. As another example, creep strain for a given material may be more when exposed to the same stress for a longer period of time when compared to a shorter period of time. Accordingly, a rate of deformation of a material due to creep strain may be a function of the material's properties, exposure time, exposure temperature, and an applied structural load.

A creep threshold may be specific to a device (e.g., an auto-injector) and/or one or more components of the device. The creep threshold for a device and/or one or more components may be a creep strain value at or based on a level that the deformation of the device and/or one or more components can no longer perform its given function.

According to certain embodiments, a simulation component may generate a linear device model of a medical device. The linear device model may be based on relationships between a plurality of components of the medical device. The simulation component may generate the linear device model based on determined or sensed attributes of the medical device. For example, a sensor may be used to determine the relationship between torque and axial force of a leadscrew in the medical device. The simulation component may create the linear device model based on some or all of determined or sensed attributes and their relationships to each other.

The linear device model generated in accordance with certain embodiments disclosed herein may include linear attributes to minimize simulation time. For example, the relationship between torque and axial force of a leadscrew may be a linear attribute such that a change in axial force is matched with a linear change in torque. The linear attributes applied herein may each have a change amount or "slope," generally referred to herein as a coefficient. For example, the coefficient for the torque to axial force ratio may be referred to as C2+C3 which value is indicative of a slope of the linear attribute.

According to certain embodiments, the simulation component may generate a distribution of outputs (e.g., force, speed, current torque, voltage, etc.) for the medical device and/or its components. The distribution of outputs may be simulated outputs that the medical device or its components may experience based on a set of inputs, and may be generated using the linear device model. The inputs may include a distribution of inputs for the coefficients of the linear device model as well as other inputs (e.g., drug viscosity). For example, the linear device model may be used to simulate a plurality of potential force outputs of a given medical device. In a first instance, a first distribution of coefficients may be applied to the linear device model along with a supply voltage and the linear device model may output a distribution of scalar values each based on an iterative simulation (e.g., a force value, a speed value, a current value, a torque value, a voltage value, etc.). Simulations may be performed a plurality of times (e.g., approximately thousands of times, approximately tens of thousands of times, approximately hundreds of thousands of times, approximately two million times, approximately between one million and four million times, approximately between five hundred thousand and five million times, etc.) to output the distribution of output scalar values that correspond to each of the outputs (e.g., a force value, a speed value, a current value, a torque value, a voltage value, etc.). The outputs may be used to determine whether a given design for a medical device meets one or more quality or use criteria. Alternatively, or in addition, the outputs may be used to determine testing parameters for the given medical device. Auto-Injector Simulations disclosed herein may be based on an auto-injector or auto-injector components. Embodiments of the present disclosure may be used in addition to and/or in combination with aspects of International Application No.

Figure 1A:
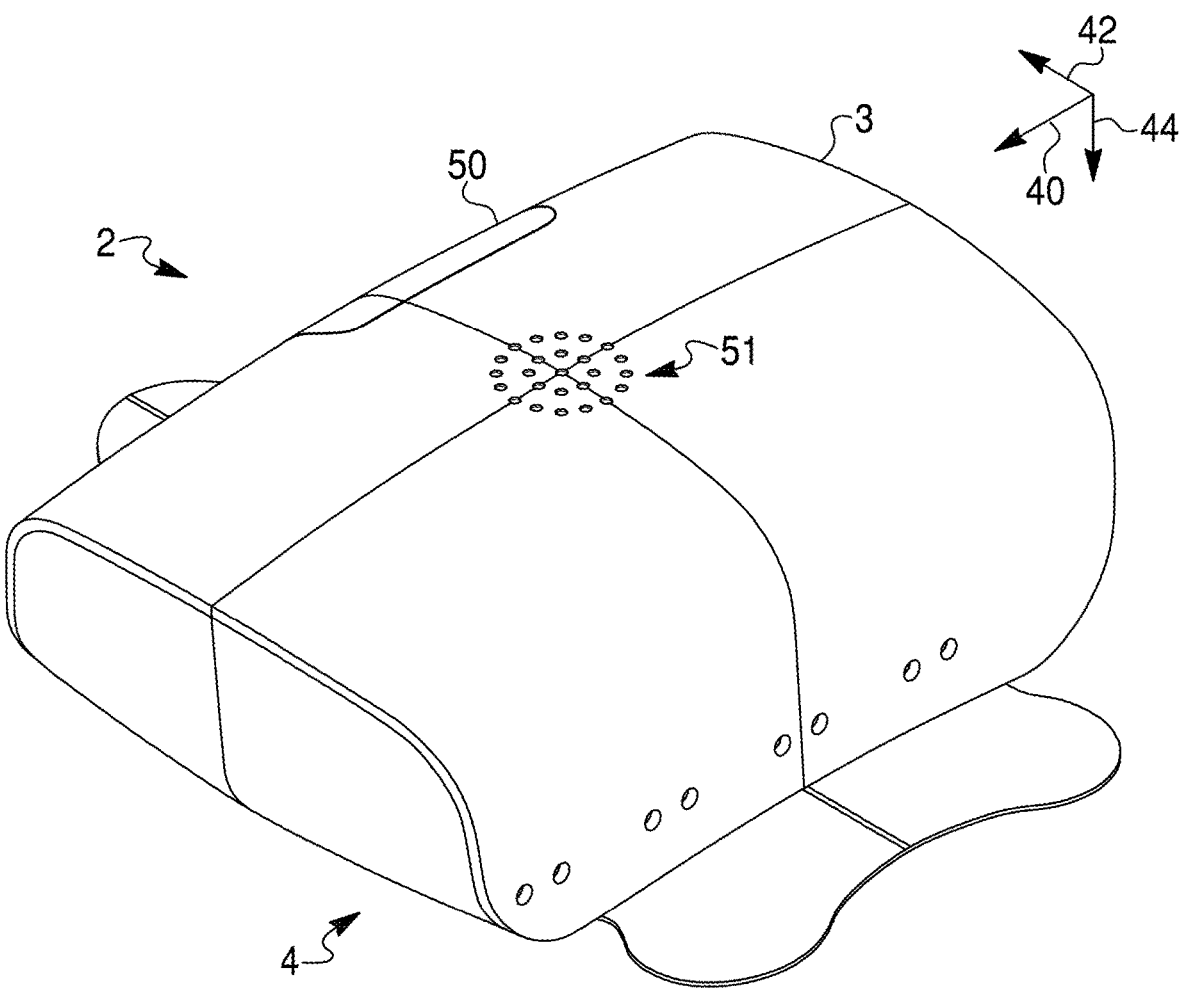
FIG. 1A is a perspective view of an auto-injector, according to an example of the disclosure.
Figure 1B:
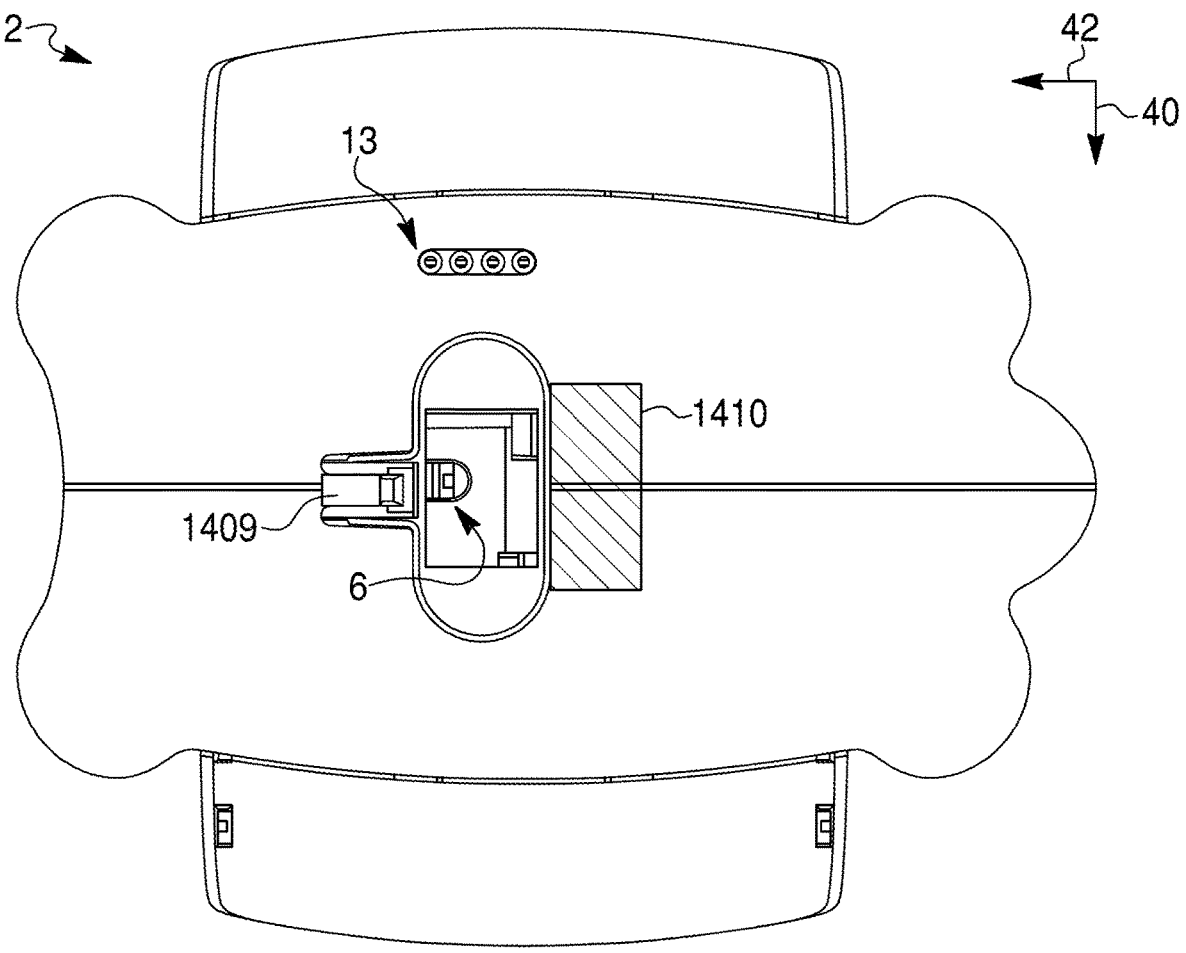
FIG. 1B is a bottom view of the auto-injector of FIG. 1A, according to an example of the disclosure.
Figure 1C:
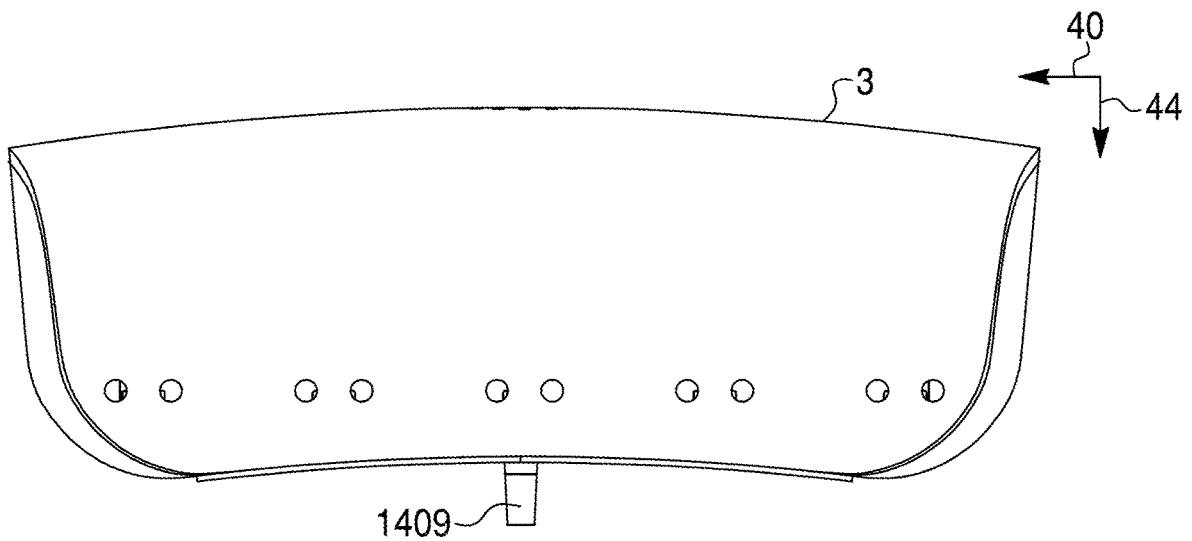
FIG. 1C is a side view of the auto-injector of FIG. 1A, according to an example of the disclosure.
Figure 2:
FIG. 2 is an exploded view of the auto-injector of FIG. 11, according to an example of the disclosure.

PCT/US2018/031077, which is incorporated by reference in its entirety herein. PCT/US2018/031077 discloses an example of an auto-injector 2 that is also is shown in FIGS. 1A-2 herein. It also is contemplated that simulations contemplated herein could be performed based on other suitable auto-injectors. Auto-injector 2 may include a housing 3 having a tissue-engaging (e.g., bottom) surface 4 through which a needle may be deployed and retracted via an opening 6 as shown in FIG. 1B. An activating switch 1409, as shown in FIG. 1B and FIG. 1C, may be disposed on tissue-engaging surface 4, and may be configured to activate auto-injector 2, or otherwise place auto-injector 2 in a "ready" mode. A touch sensor 1410 also may be disposed on tissue-engaging surface 4, and may be configured to help a controller of auto-injector 2 determine whether auto-injector 2 is disposed on the skin of a user (indicating that the auto-injector should fire or otherwise deploy a needle), or whether activating switch 1409 was improperly triggered (indicating that operation of auto-injector 2 should be stopped). A connecting port 13 also may be disposed on tissue-engaging surface 4 to facilitate programming of auto-injector 2. Auto-injector 2 may have any suitable dimensions suitable to enable portability and self-attachment by a user.

As shown in FIG. 2, a shuttle 340 (e.g., a shuttle actuator) may be configured to move driver 320 via a deployment gear. Shuttle 340 may be coupled to a resilient member (e.g., a spring).

An adhesive patch 12 may be coupled to tissue-engaging surface 4 to help secure auto-injector 2 to a user's body (e.g., skin).
Creep As disclosed herein, a medical device, such as auto-injector 2, may experience creep strain as a result of one or more stresses applied to the medical device. The stresses may be internal stresses such as those exerted by a spring, a component on another component, a plunger, or the like (e.g., a stress exerted by shuttle 340). A technique for identifying the creep strain profile of a given device or component is shown in FIG. 3A. Creep strain predictions may be used to build time hardening models, may be applied to stress fields on pre-loaded components, may be used to predict material (e.g., plastic) deflection of features, or the like. Creep strain on a physical device may be analyzed to determine trend lines based on different strain values, as shown in chart 302. Chart 302 plots the different creep strains measured for a given component (e.g., shuttle 340) shown in image 304, at five different varying strain levels. Each of the five trend lines in chart 302 may be determined by applying each of five different strain levels for the same duration of time. The strain amounts that correspond to a given trend line can be plotted using Equation 1 (labeled as 302A):

$$\dot{\varepsilon} C_1 \sigma^{C_2} t^{C_3} \tag{1}$$

As disclosed above in Equation 1, the creep strain is determined based on a first coefficient $C_1$, second coefficient $C_2$, time t, and third coefficient $C_3$. Coefficients $C_1$, $C_2$, and $C_3$ may be coefficients as further discussed herein.

Creep strain levels for a component at a given time or over time may be shown as overlaid on the component. The example provided in image 304 shows the strain points (e.g., the creep strains plotted in chart 302) overlaid on the component corresponding to the creep strains plotted in chart 302. In image 304, the different amounts of creep strain experienced at different areas of the shuttle 340 are shown by different shades.

The creep strain plotted in chart 302, based on sensed creep strain at different strain levels over time, may be used to generate a creep strain profile 306 for the component shown in image 304. The creep strain profile 306 shows displacement over time and may correspond to the creep strain that the component shown in image 304 may experience over time, based on strains applied to the component as the component is used in auto-injector 2 at ambient conditions. The creep strain profile 306 may be used to determine whether the component shown in image 304 meets use and/or quality criteria either independently or as a component of auto-injector 2.

Figure 3C:
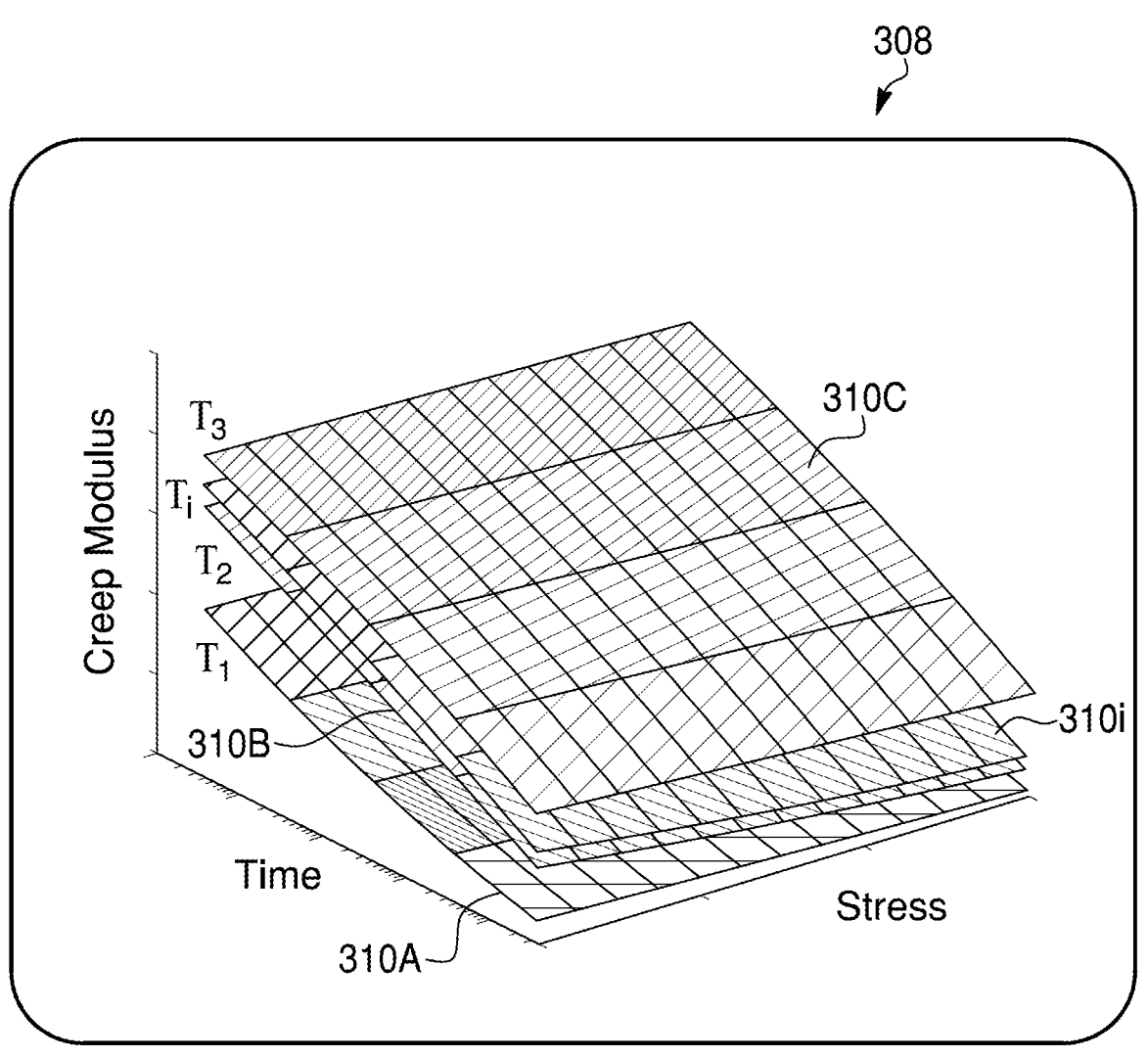
FIG. 3C includes a chart of a temperature based creep modulus in view of time and stress, according to an example of the disclosure.

According to another implementation of the disclosed subject matter, a predictive temperature stress and time creep modulus may be generated for a device or component, such as for example, an auto-injector. FIG. 3B shows a process 307 for generating a predictive temperature stress and time creep modulus that can be used for accelerated age testing. One or more aspects of process 307 may be implemented using one or more of a computer, processor, memory, and the like, as further disclosed herein. At 307A of process 307, creep modulus data (e.g., raw creep strain data) may be received by the computer, processor, memory, or the like. The creep modulus data may include creep strain values as they are related to a duration of stress (e.g., time) and an amount of stress, for a plurality of temperatures. FIG. 3C shows a chart 308 with a plurality of creep strain surfaces 310A, 310B, and 310C. Creep strain surfaces 310A, 310B, and 310C are visual representations of the creep strain for a given device or component, as factors of durations of stress and amounts of stress, at varying temperatures (e.g., $T_1$, $T_2$, and $T_3$). According to an implementation, raw creep strain data may be predicted (e.g., using simulations) or generated (e.g., based on sensed creep strains) for a device or component, based on the techniques disclosed herein. The creep strain surfaces 310A, 3106, and 310C each show a visual representation of the raw creep strain data over time and over different stress amounts. The raw creep strain data may be used to determine creep strains as a factor of time and stress, for different temperatures (e.g., $T_1$, $T_2$, and $T_3$). For example, the visual representation shown in surface 310A shows the amount of creep strain a given component may experience at various different stress levels based on the amount of time each stress level is applied to the component, at temperature $T_1$.

At 307B of process 307, interpolation (e.g., 3D interpolation) may be performed on the raw creep strain data for a given device or component to generate a predictive temperature stress and time creep modulus based on the given device or component. The predictive temperature stress and time creep modulus generated based on the given device or component be used to identify a creep strain for different stress amounts, durations of stress, and temperatures (e.g., as visually represented using surface 310i) for the given device or component or one or more other devices or components (e.g., a component that is similar to the given device or component).

According to an implementation, the interpolation performed at 307B of process 307 may be a trilinear interpolation. The trilinear interpolation may be a multivariate interpolation on a 3D regular grid. The trilinear interpolation may approximate the value of a function at an intermediate point (e.g., an x, y, z coordinate of chart 308) within a local axial rectangular prism linearly, using function data on lattice points. The predictive temperature stress and time creep modulus generated using the interpolation performed at 307B may be used to identify a creep strain as a function of stress and time for any applicable temperature $T_i$. Accordingly, the generated predictive temperature stress and time creep modulus may be used to output creep strains based on a temperature, amount of time, and stress. Alternatively, the generated predictive temperature stress and time creep modulus may be used to output a temperature needed to reach a given creep strain based on a given amount of time and a given amount of stress. Alternatively, the generated predictive temperature stress and time creep modulus may be used to output a time needed to reach a given creep strain based on a given amount of stress at a given temperature.

A medical device such as auto-injector 2 and/or one or more components of the medical device may be tested for degradation. Degradation may include material degradation as well as creep strain degradation. Material degradation (e.g., the amount a plastic degrades) may occur, for example, by the process of corrosion and oxidation in wet and dry environments, respectively. Material degradation may be tested to identify the effects of water vapor on a material over time. Material degradation may be tested using an accelerated aging chamber. Accelerated aging testing may be implemented using aggravated conditions of heat, humidity, oxygen, sunlight, vibration, and the like to speed up the normal aging processes of a given device, component, or material. It may be used to help determine the long-term effects of expected levels of stress within a shorter time. The material degradation based on an amount of time spent in an accelerated aging chamber may be correlated to the amount of time in ambient conditions based on Arrhenius relationships that map the ambient conditions to accelerated conditions. However, no such relationships exist for creep strain degradation.

Figure 3D:
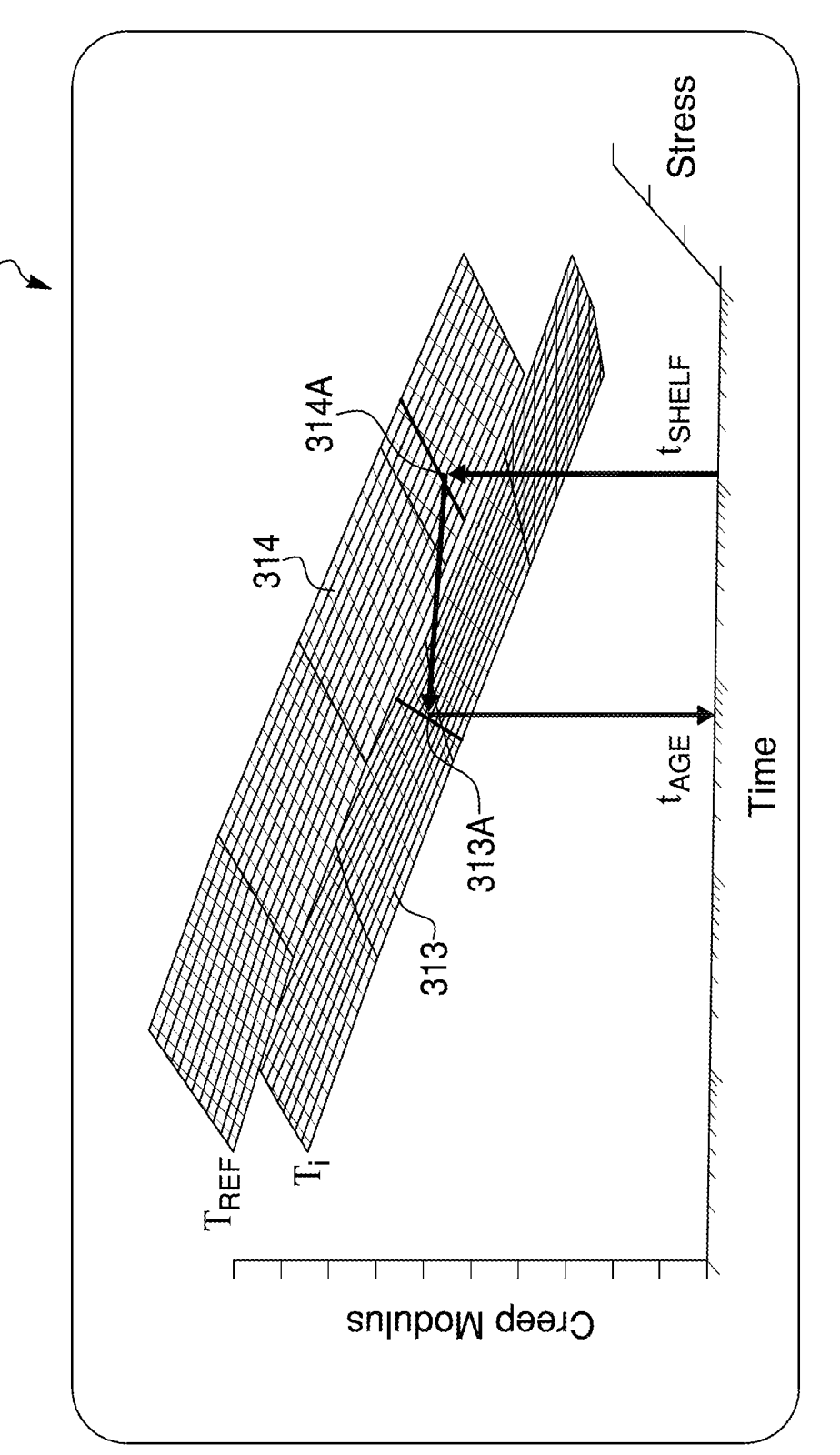
FIG. 3D includes a diagram of a predictive temperature stress and time creep modulus, according to an example of the disclosure.

At 307C of process 307, variables may be identified for accelerated age testing of a given device or component. The variables may be a temperature, an amount of time, and/or an amount of strain (e.g., to mimic creep strain over a given period of time, a given stress, and/or an ambient temperature). FIG. 3D shows a diagram 312 for identifying variables in accordance with techniques disclosed herein. Diagram 312 is a visual representation of a predictive temperature stress and time creep modulus generated at 307B, based on interpolating the raw creep modulus data received at 307A. The predictive temperature stress and time creep modulus generated at 307B and shown in FIG. 3D may be used to identify accelerated testing variables (e.g., temperature, time, stress) to mimic the creep strains at a reference temperature $T_{REF}$. Creep strain surface 314 is visual representation of the predictive temperature stress and time creep modulus for $T_{REF}$. According to an example, $T_{REF}$ may correspond to an ambient temperature or a temperature associated with use and/or storage of the given device or component. As shown in FIG. 3D, $t_{SHELF}$ may correspond to, for example, an expected shelf-life for the given device or component. However, it will be understood that $t_{SHELF}$ may be any applicable duration of time. A target point 314A may correspond to a reference creep strain and may, for example, correspond to a target shelf-life time $t_{SHELF}$ of the given device or component, at temperature $T_{REF}$, and having an anticipated amount of stress corresponding to point 314A. The anticipated amount of stress may be determined, for example, based on a creep strain sensor that detects stress experienced by the device or component during storage or during operation.

As discussed herein, accelerated testing may be used to confirm whether the given device or component meets a creep strain quality criteria. The device or component that is tested using accelerated testing may be the same device or component for which a creep modulus is received at 307A of FIG. 3C, based on which the predictive temperature stress and time creep modulus is generated at 307B. Alternatively, the device or component that is tested using accelerated testing may be similar to the device or component for which a creep modulus is received at 307A of FIG. 3C. For example, the device or component that is tested using accelerated testing may be a device manufactured based on the same design as the device or component for which a creep modulus is received at 307A of FIG. 3C. The creep strain experienced using the accelerated testing may be compared to an expected creep strain (e.g., the creep strain at reference point 314A).

As discussed, accelerated testing may be conducted by receiving raw creep modulus data (e.g., as shown in FIG. 3C) for a device or component. A predictive temperature stress and time creep modulus generated at 307B (e.g., as visually represented in FIG. 3D) may be generated. The predictive temperature stress and time creep modulus generated at 307B may be used to output an accelerated temperature, an accelerated time, and/or an accelerated stress based on a reference point (e.g., reference point 314A of a predictive temperature stress and time creep modulus for reference temperature $T_{REF}$).

The accelerated testing may be performed using an accelerated temperature, accelerated time, and accelerated stress determined using the predictive temperature stress and time creep modulus. The accelerated testing may be performed under the accelerated temperature and accelerated stress and an accelerated testing creep strain experienced by the given device or component may be determined, after the accelerated time. The accelerated testing creep strain may be compared to the reference creep strain (e.g. at reference point 314A of a predictive temperature stress and time creep modulus for reference temperature $T_{REF}$). If the accelerated testing creep strain is within a threshold creep strain amount of the reference creep strain, the device or component may be approved and/or the predictive temperature stress and time creep modulus may be verified. For example, an approval indication may be generated approving the device or component or approving the predictive temperature stress and time creep modulus. If the accelerated testing creep strain is not within a threshold creep amount of the reference creep strain, the device or component may be rejected and/or the predictive temperature stress and time creep modulus may not be verified. For example, a rejection indication may be generated rejecting the device or component or rejecting the predictive temperature stress and time creep modulus. An approved device or component may be approved for example, for use by a user or provider. A verified predictive temperature stress and time creep modulus may be used to predict creep strains for a designed device or component. According to an indication, accelerated testing to validate a predictive temperature stress and time creep modulus may be conducted using a component. The component may be a simple component, when compared to one or more other components or a device with multiple components. The component may have limited stress points or changes in stress points such that the predictive temperature stress and time creep modulus may be validated with a limited number of external variables.

Identification of one or more variables using a predictive temperature stress and time creep modulus is further disclosed herein. As shown in FIG. 3D, the creep strain at reference point 314A may correspond to an accelerated point 313A on a $T_i$ creep strain surface 313. The $T_i$ creep strain surface 313 may be a visual representation of the predictive temperature stress and time creep modulus for any arbitrary temperature $T_i$. Accordingly, the creep strain at reference point 314A may be mimicked at a time $t_{AGE}$ that is less than time $t_{SHELF}$, at an accelerated temperature $T_i$, and stress amounts indicated by the line at accelerated point 313A.

As an example, the reference point 314A may correspond to reference creep strain at a three year shelf-life $t_{SHELF}$. At the target point 314A, the amount of creep strain may be based on to the amount of stress indicated by the stress line at target point 314A. In order to mimic the creep strain at reference point 314A, the predictive temperature stress and time creep modulus may be used to output an accelerated temperature $T_i$ such that an amount of creep strain at the accelerated point 313A at a three month accelerated time $t_{AGE}$ is the same as the creep strain at reference point 314A at the temperature $T_{REF}$ at time $t_{SHELF}$. Accordingly, creep strain surface 313 at an accelerated temperature $T_i$ may be identified and may be expected to have a creep strain at accelerated point 313A (e.g., at the three month time $t_{AGE}$) that mimics the creep strain at reference point 314A. Based on the temperature, stress, and time variables depicted using creep strain surface 313 a given device or component may be placed in an accelerated chamber for a time $t_{AGE}$ (e.g., three months) at temperature $T_i$, at a stress level determined based on the stress line at accelerated point 313A and/or stress line at reference point 314A. According to another example, accelerated time $t_{AGE}$ may be output by the predictive temperature stress and time creep modulus shown in FIG. 3D. The accelerated time $t_{AGE}$ may be output based on the reference creep strain at reference point 314A, the reference stress indicated at target point 314A, and a given temperature $T_i$. For example, an accelerated chamber may be configured to operate at an accelerated temperature $T_i$. To mimic the conditions at reference point 314A, the predictive temperature stress and time creep modulus of FIG. 3D may be used to identify the accelerated time $t_{AGE}$ required to mimic the conditions at reference point 314A using reference stress at reference point 314A and accelerated temperature $T_i$.

At 307D of process 307, age testing may be conducted based on the variables identified for accelerated age testing. The age testing may be conducted by placing the given item in an accelerated age chamber set at temperature $T_i$ for the time $t_{AGE}$, and at a stress level determined based on the line at accelerated point 313A and/or at reference point 314A. According to an example, a first medical device may be used to determine the predictive temperature stress and time creep modulus as described at 307A-307C. At 307D, a second medical device may be age tested based on the predictive temperature stress and time creep modulus determined using the first medical device. In this example, the first medical device may be a control medical device and the second medical device may be manufactured based on the design of the first medical device. The second medical device may be tested using the age testing disclosed herein, to ensure it conforms to the parameters established using the first medical device. Alternatively or in addition, one or more variable for an aging test may be determined using a reference stress (e.g., a computed stress or stress field) and the predictive temperature stress and time creep modulus.

Linear Device Model for Improved Simulation

According to embodiments of the disclosed subject matter, a plurality of simulations may be generated using a linear device model. A simulation component may generate the plurality of simulations and may include or may be one or more of a processor, controller, microcontroller, memory, or the like. The simulation component may generate the simulations based on a linear device model of a device (e.g., auto-injector 2). The linear device model may be generated by the simulation component or may be provided to the simulation component. The linear device model may be based on relationships between a plurality of components of the device.

The plurality of simulations may be based on attributes of the device as defined based on the relationships between the components of the device. The plurality of simulations may output how a physical version of the device operates (e.g., how long an injection duration would be if using the device with a drug with a given viscosity). The plurality of simulations may facilitate a design of experiment (DOE) to generate multiple outputs based on a number of different variables. The plurality of simulations may output distributions of one or more scalar values associated with the device. The distributions may be compared to one or more use or quality criteria and/or may be used to test the device to ensure device operation across the distribution. For example, as further discussed herein, the simulations may output a distribution of an amount of force that an auto-injector will experience. The distribution of an amount of force may be determined using simulations performed based on the relationships between components of the device such as a battery, electronic control, motor/gearbox, leadscrew, cartridge, plunger, and fluid path. The distribution may range from a lower threshold to an upper threshold. Accordingly, the lower or upper threshold may be compared to quality and/or use criteria to ensure that an attribute (e.g., force) experienced by the auto-injector is within an acceptable range. Alternatively, or additionally, a physical version of the auto-injector may be tested under the lower or upper threshold of the attribute (e.g., upper threshold of force), to ensure compliance (e.g., durability) at that lower or upper threshold.

As shown in FIGS. 1A-1C, auto-injector 2 may include a plurality of components. One or more of the components may interact with one or more other components of auto-injector 2. The interactions may define a plurality of relationships between the components. For example, shuttle 340 may move based on force applied by a motor that uses a gearbox to transfer the force. The motor may be driven using a battery and electric control component. The voltage of the motor may be provided by the battery via the electronic control such that the motor and gearbox operate at a given motor current and produce a given motor torque. Accordingly, the voltage and current provided by the battery and electronic control component may be related to the motor speed and torque.

Figure 4:
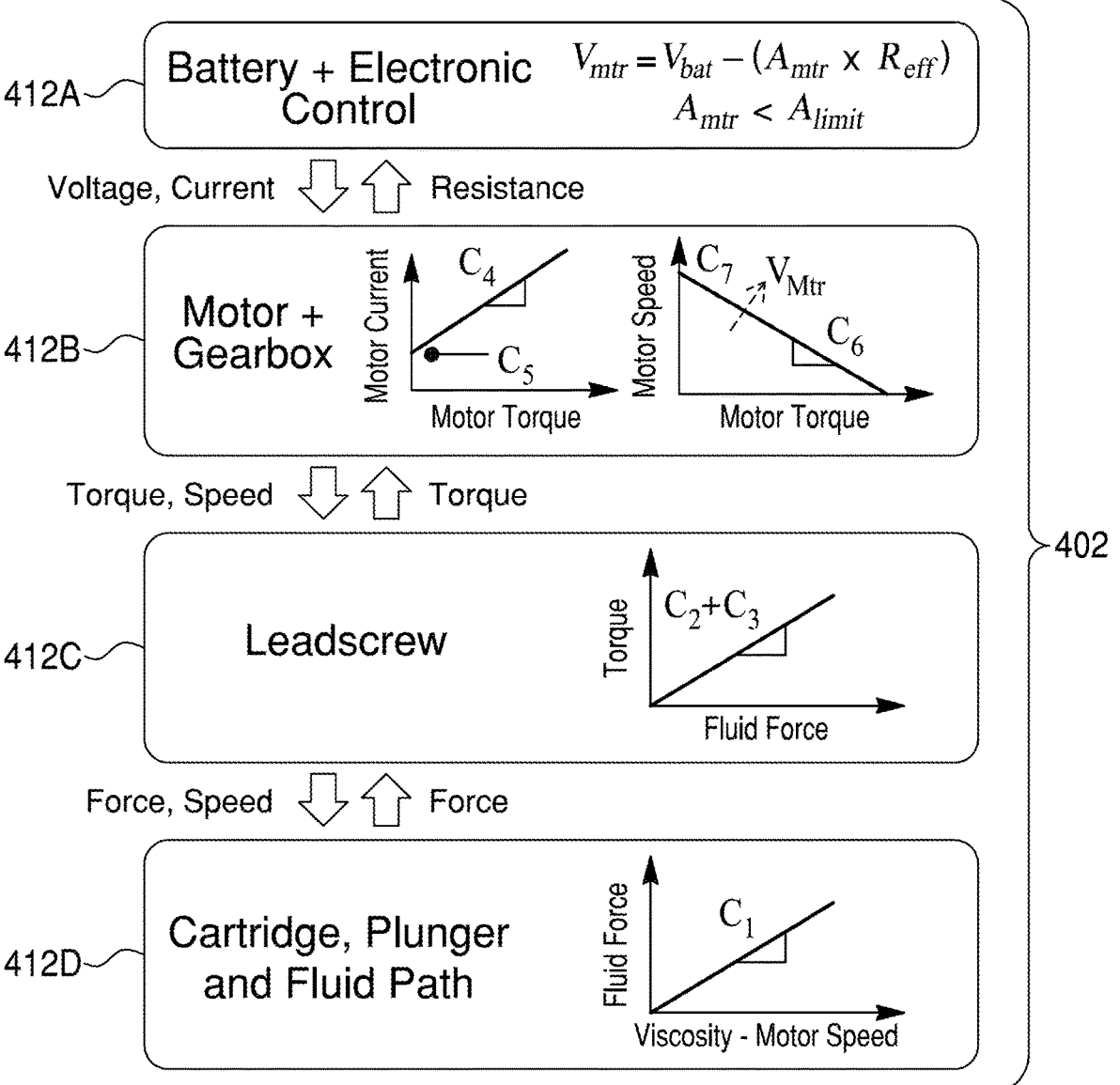
FIG. 4 includes components of a linear device model, according to an example of the disclosure.

FIG. 4 shows a plurality of relationships 412A, 412B, 412C, and 412D that, together, form linear device model 402 for an auto-injector (e.g., auto-injector 2). Although a linear device model (e.g., linear device model 402) is shown herein, it will be understood that a linear device model may refer to a linearized model (e.g., of a non-linear system), a reduced model and/or quasi-linear device model/quasi-steady state model that may be applied in accordance with the techniques disclosed herein. For example, a linearized model may be generated by creating a linear approximation of a nonlinear system. A quasi-steady state model may be used to approximate operation of an unsteady system by applying discrete points in time. A linear device model may predict study state parameters based on one or more coefficients, as disclosed. The linear device model may be computationally efficient, such that large-scale design of experiment simulations be executed (e.g., using Monte Carlo simulations) with limited computational resources.

For example, over ten thousand simulations may be conducted in less than one hour (e.g., using commercially available computing devices). As another example, over two million simulations may be conducted in less than one hour (e.g., using commercially available computing devices). As another example, approximately one hundred thousand simulations may be conducted in less than thirty seconds.

Each of the relationships 412A, 412B, 412C, and 412D characterize how a corresponding component operates. For example, relationships 412A define the voltages and currents associated with an auto-injector battery and electronic control. Relationships 412A are shown below in Equation 2 and Equation 3:

$$V_{mtr} = V_{bat} - (A_{mtr} \times R_{eff}) \tag{2}$$

$$A_{mtr} < A_{limit} \tag{3}$$

The charts showing relationships 412B define the motor current in view of the motor torque and the motor speed in view of the motor torque of the auto-injector's motor and gearbox. As shown, the motor voltage $V_{mtr}$ of Equation 2 for the auto-injector battery and electronic control is related to the relationships 412B as it defines the motor speed and motor torque of the motor and gearbox (e.g., the motor speed is dependent on the motor voltage $V_{mtr}$). Additionally, the motor torque of the motor and gear box of relationship 412B is related to the motor current ($A_{mtr}$) of Equation 2 and Equation 3 of relationship 412A. The motor torque of the motor and gearbox in relationship 412B is related to the torque of the leadscrew in relationship 412C. The axial force of the leadscrew in relationship 412C is related to the fluid force of the cartridge, plunger, and fluid path of relationship 412D. The fluid force of the cartridge, plunger, and fluid path of relationship 412D is affected by the motor speed of the motor and gearbox of relationship 412B. Accordingly, each of the relationships 412A, 412B, 412C, and 412D of linear device model 402 are related to each other and model the operation of an auto-injector.

The linear relationships 412A, 412B, 412C, and 412D of linear device model 402 may both model the corresponding auto-injector in sufficient detail and also enable simulations based on the linear device model 402 to perform at a faster rate in comparison to simulations performed on non-linear device models. By performing faster simulations using linear device model 402, the amount of time required to determine operation of the auto-injector and performance metrics of the auto-injector may be reduced. Additionally, by performing faster simulations, determinations regarding how to control the auto-injector using an electronic controller may also be determined faster and/or larger populations may be studied (e.g., using a Monte Carlo analysis).

As shown in the linear device model 402, each of the relationships 412B, 412C, and 412D may be based on coefficients C1 through C7. The coefficients C1 through C7 may correspond a change amount or "slope" of linear attributes of the auto-injector. Coefficient C1 may be determined based on a combination of conditions such as the restriction amount of a needle that fluid is pushed through and/or a pitch of a leadscrew. C2+C3 may correspond to the torque the leadscrew. C4 may be the slope of the relationship between the motor current and motor torque. C5 may be a y-intercept corresponding to a no-load torque such that C5 is the amount of current that it takes for the motor of the auto-injector to spin with no load applied to the shaft (i.e., overcoming internal friction, electrical resistances, etc.). C6 may be the slope of the relationship between the motor torque and motor speed. C7 may be a no-load speed scaled by an input voltage.

According to an example, simulations generated based on the linear device model 402 may be determined by generating a matrix based on the relationships 412A, 412B, 412C, and 412D. The matrix may then be inverted to provide a simulation component. Multiple simulations may be generated based on modifying variables, such as one or more of the coefficients C1 through C7, as further disclosed herein.

Figure 5A:
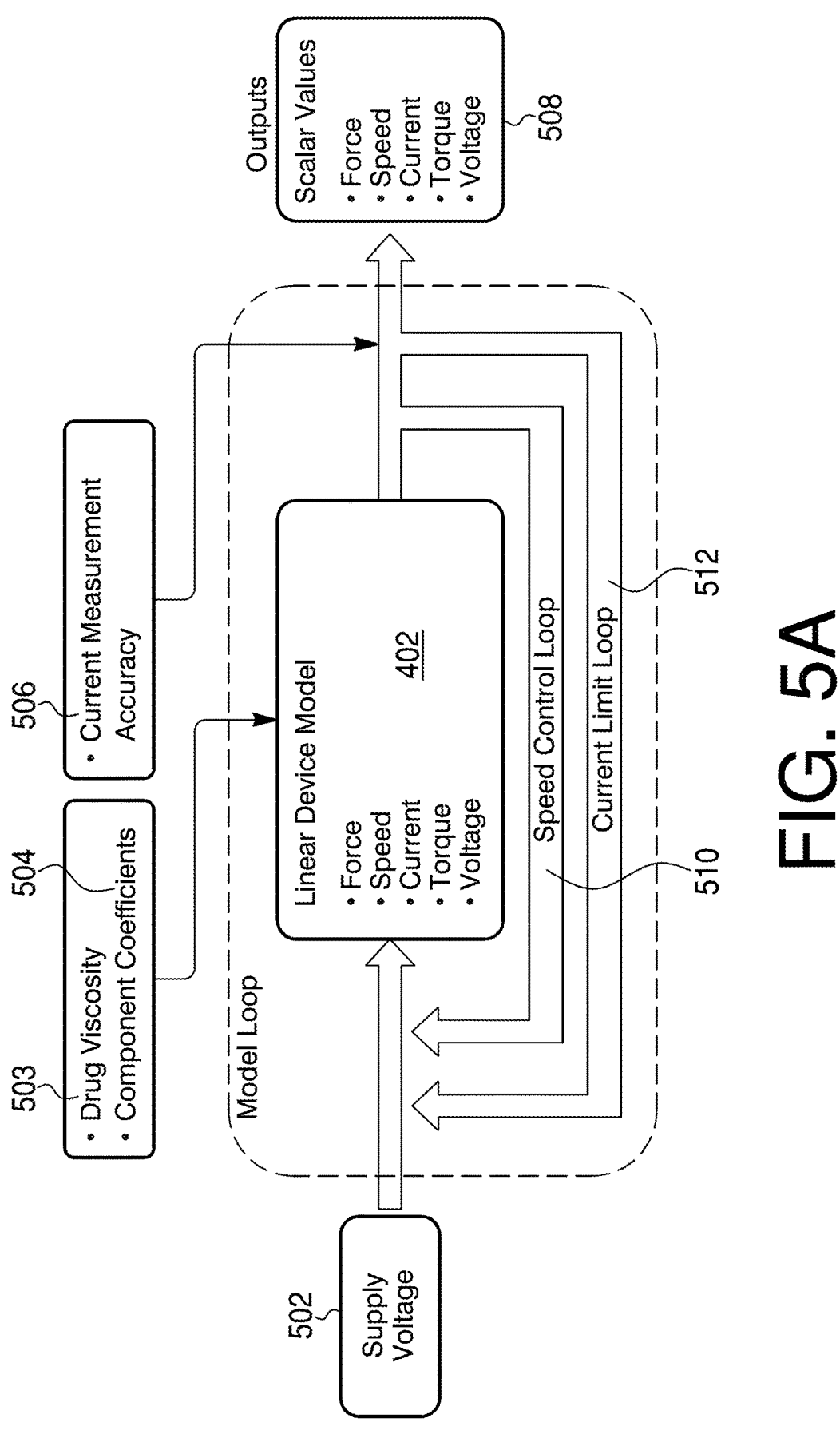
FIG. 5A includes a system model, according to an example of the disclosure.

FIG. 5A shows a system model structure that applies the linear device model 402 of FIG. 4. The linear device model 402 may receive a plurality of inputs including a supply voltage 502, a speed control loop output 510, a current limit loop output 512, drug viscosity 503, and component coefficients 504. The supply voltage 502 may be the voltage output from a battery (e.g., the battery corresponding to relationships 412A) or other voltage generator. The component coefficients 504 may correspond to the coefficients C1 through C7 discussed in relation to FIG. 4. The speed control loop output 510 and the current limit loop output 512 may be used based on a function of a random combination of inputs, as further discussed herein. For example, one or both of the speed control loop output 510 and the current limit loop output 512 may be used if a scalar output exceeds a threshold such that either the speed or current may be reduced via a respective loop to maintain the given scalar output within the threshold. Accordingly, the speed control loop output 510 and the current limit loop output 512 may be used to adjust the supply voltage 502 when an output 508 is outside given thresholds. Current measurement accuracy 506 may also be a randomized input to account for variances in current measurements. The current measurement accuracy 506 may result in a more realistic distribution of outputs 508, as further discussed herein.

Figure 5B:
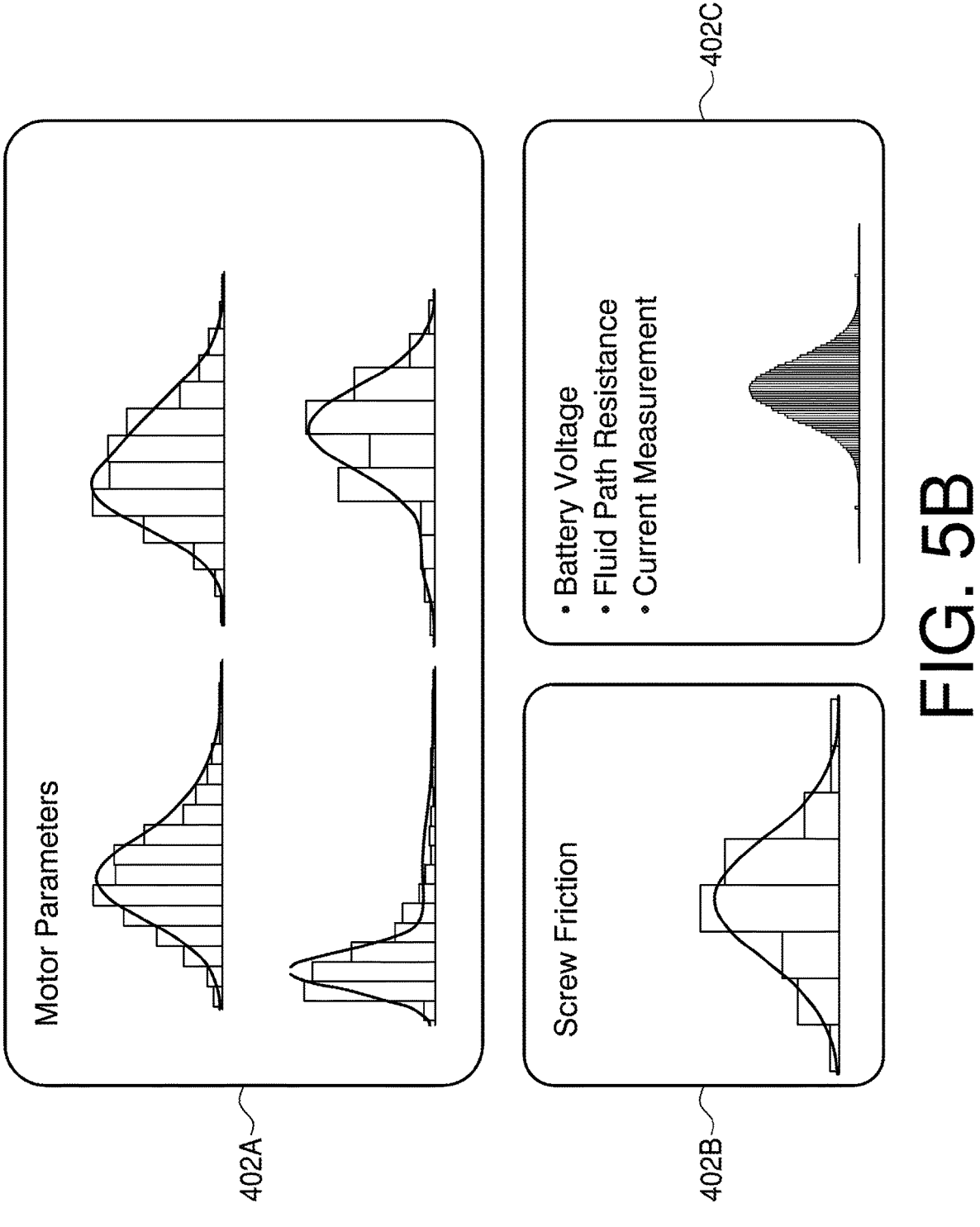
FIG. 5B includes inputs to the system model of FIG. 5A, according to an example of the disclosure.

A set of component coefficients 504 may be applied to the linear device model 402 for each generated simulation. The component coefficients 504 used for each given simulation may be selected using a Monte Carlo simulation where the Monte Carlo simulation outputs a value for each coefficient (i.e., for coefficients C1 through C7). A Monte Carlo simulation may be a computerized technique that accounts for distribution probabilities in decision making. The value for each given coefficient (i.e., from coefficients C1 through C7) for each simulation may be selected from a distribution of potential values for the corresponding coefficient. A probability distribution function may be used by a Monte Carlo simulation to select a random value for a coefficient. The distribution function for a given coefficient may be determined based on variances of that coefficient in the auto-injector (e.g., variance due to material properties, manufacturing differences, use, etc.). The random value may be selected from a weighted distribution curve for each given coefficient. For example, FIG. 5B shows motor parameters 402A for the motor of the auto-injector for which the simulations are generated. The motor parameters may correspond to coefficients C4 and C5 in the linear device model 402. The top left chart shows a distribution of outputs that may correspond to, for example, C4 such that the Monte Carlo simulation may provide a value for coefficient C4 based on the probability curve shown in the top left chart of parameters 402A. Accordingly, the Monte Carlo simulation may provide a value for coefficient C4 that is found towards the middle of the top left distribution chart more often than values that are found towards the edges of the top left distribution chart.

Each simulation of a plurality of simulations may use one or more different values for each component coefficient 504. For example, over approximately ten thousand to approximately two million or more simulations, a large plurality of combinations of coefficient values for component coefficients 504 may be provided to the linear device model 402.

The linear device model 402 may also receive values of drug viscosity 503 output by a Monte Carlo simulation based on a distribution curve of possible drug viscosities. The distribution curve of drug viscosities may be determined based at least in part on drug properties at different temperatures. Additional inputs to the linear device model 402 may include screw friction as shown in distribution 402B of FIG. 5B, as well as a battery voltage, fluid path resistance, and current measurement inputs 402C of FIG. 5B. The screw friction shown in distribution 402B may correspond to coefficients C2 and C3 of the linear device model 402. The fluid path resistance may correspond to coefficient C1 of the linear device model 402.

Figure 6:
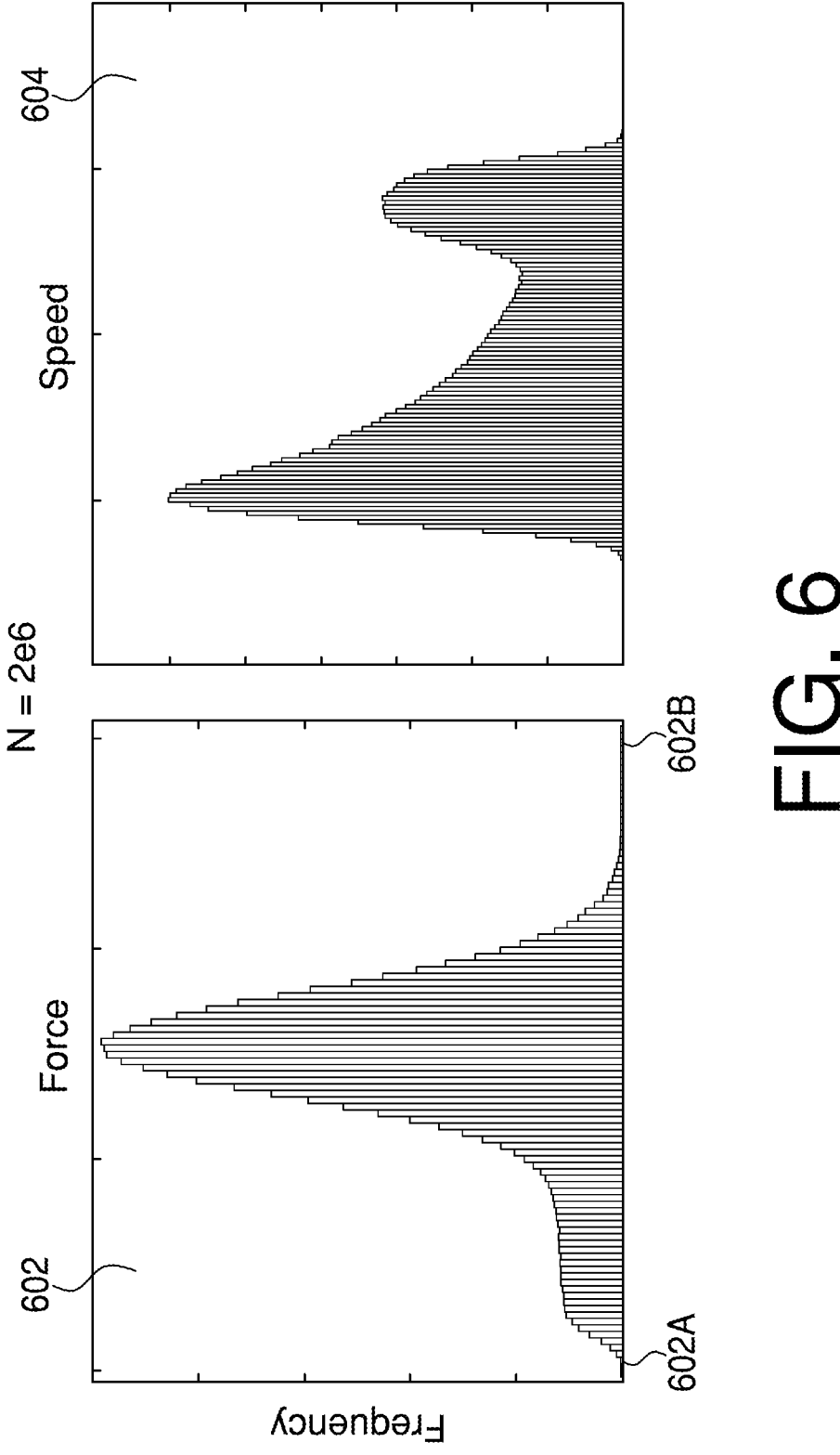
FIG. 6 includes outputs from the system model of FIG. 5A, according to an example of the disclosure.

The output 508 of the linear device model 402 for each simulation may include scalar values such as force values, speed values, current values, torque values, voltage values, or the like. For example, FIG. 6 shows two scalar value outputs including a force output distribution 602 and a speed output distribution 604. Each of the two scalar value output distributions may be output by the linear device model 402, as shown in FIGS. 4 and 5A. The force output distribution 602 and speed output distribution 604 are based on approximately two million simulations, as indicated by N=2e6 in FIG. 6. As shown in FIG. 6, the force output distribution 602 may range from a minimum force value 602A and a maximum force value 602B.

As an example, the force output distribution 602 may correspond to a force exhibited by the auto-injector that the linear device model 402 is based on (e.g., based on the force applied when using an auto-injector plunger). The peak of the force output distribution 602 may be 126 N (Newton). Such peak value of 126 N may be indicated by a traditional probabilistic model. However, in accordance with the techniques disclosed herein, the force output distribution 602 may be provided and may indicate that the maximum force value 602B is, for example, 200 N. According to an implementation, a maximum or minimum distribution value (e.g., maximum force value 602B) may be a value above a probability threshold (e.g., such that the maximum or minimum value does not correspond to a value with a small or an infinitesimal probability). The probability threshold may be a value or may be determined based on a number of deviations from an average value or using a different statistical variation other than standard deviation. Accordingly, one or more components of the auto-injector may be designed to withstand forces of up to 200 N instead of the peak force value of 126 N. As another example, the speed output distribution 604 may indicate the distribution of potential speeds that a drug is injected via the auto-injector. Accordingly, one or more tests may be conducted to ensure that speeds ranging from the lowest speed to the highest speed indicated by the speed output distribution 604 are acceptable speeds for use with the auto-injector.

According to implementations of the disclosed subject matter, one or more output distributions (e.g., output distribution 602, output distribution 604, etc.) may be used to approve a device or component design. An output distribution (e.g., output distribution 602 for force) may be compared to one or more threshold outputs (e.g., maximums, minimums, average, etc.). For example, model 402 may be used to generate a device model based on coefficients and based on the design of an auto-injector. The device model may be used to generate one or more output distributions (e.g., output distribution 602, output distribution 604, etc.).

The output distributions generated by the device model may be compared against one or more threshold outputs. If the outputs of the device model is within the bounds (e.g., within a range, lower than, greater than, etc.) established by the one or more threshold outputs, then the design of the auto-injector may be approved. If outputs of the device model is outside the bounds (e.g., outside a range, lower than, greater than, etc.) established by the one or more threshold outputs, then the design of the auto-injector may be rejected. Accordingly, using the techniques disclosed herein, probabilistic outputs for a device or component design may be determined based on a linear device model. The probabilistic outputs may be compared to threshold outputs to approve or reject the device or component design.

According to an implementation, the output distributions generated by the device model based may be applied to a design. The output distribution may be a normal distribution or one or more mixed distributions. Accordingly, a minimum and/or maximum output distribution may be used to update a component or device design to operate based on the minimum and/or maximum output. For example, force output distribution 602 may correspond to the force that a device component can exert. Accordingly, a device design may be updated to withstand the range of forces in the output distribution, including the minimum, peak, and/or maximum force.

Alternatively, or in addition, a device or component design may be modified based on one or more output distributions. An output distribution may be provided as feedback to a device or component and a design update may be generated based on one or more target threshold outputs. For example, a target threshold force peak for a component may be between 140-160 Newtons. The peak output force from a force output distribution (e.g., output distribution 602) from a first component design may indicate a force peak at 180 Newtons. Accordingly, the force peak at 180 Newtons may be provided as feedback to the first component design. The first component design may be updated (e.g., a shape, a material, a function, etc.) based on the feedback, and an updated distribution may be calculated. The updated distribution may indicate a force peak at approximately 144 Newtons. Accordingly, based on the updated distribution having a peak at 144 Newtons (i.e., between the target threshold force peak range of approximately 140-160 Newtons), a feedback loop may be terminated. The device model may be used to tune control parameters, which may have an effect on the distribution of force. For example, one or more coefficients of the device model may be tuned, and the tuning may result in revised force output distribution.

Figure 7:
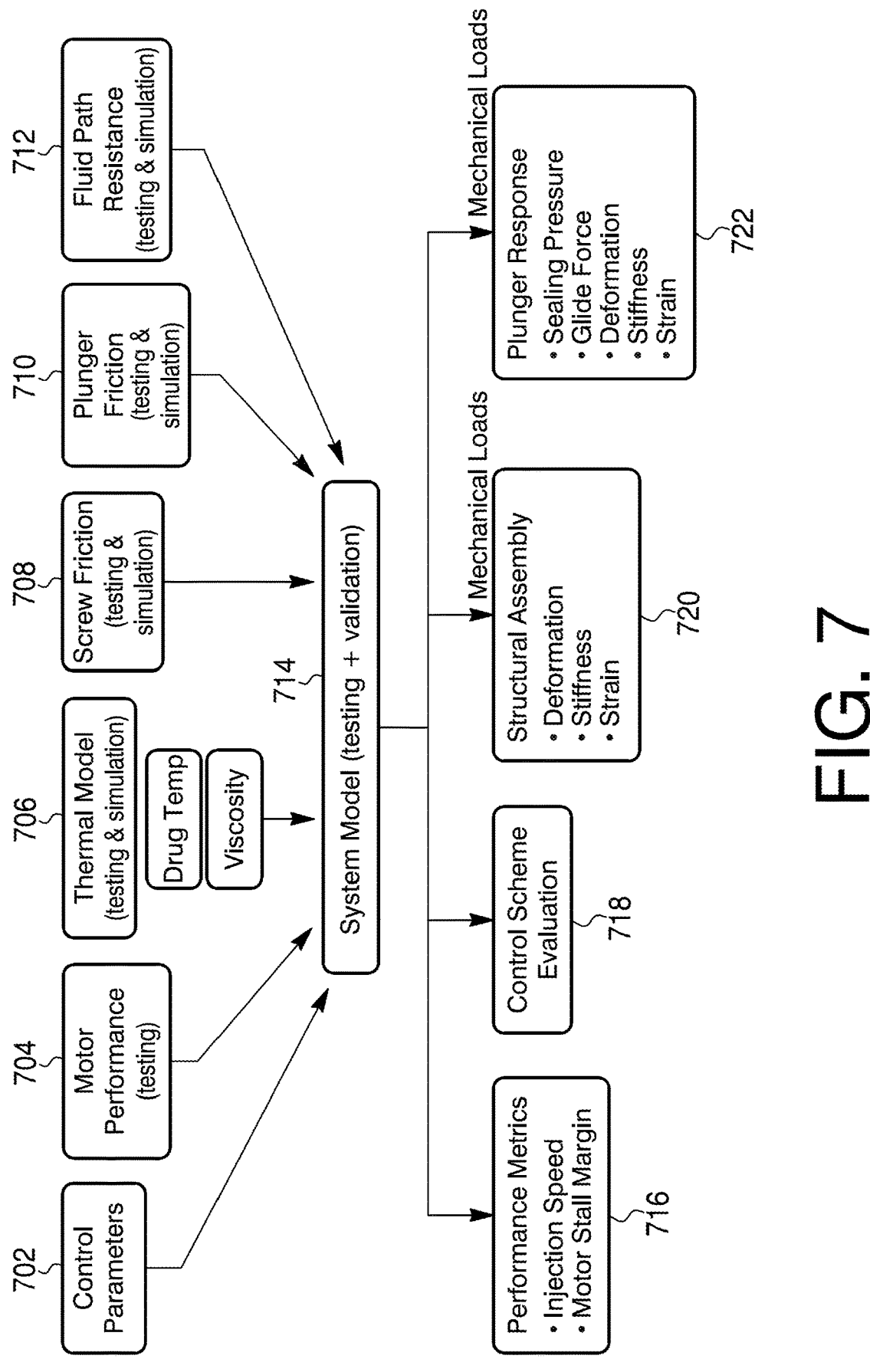
FIG. 7 shows the role of the system model of FIG. 5A in a design process, according to an example of the disclosure.

FIG. 7 shows the role of the system module of FIG. 5A in a design process. As shown in FIG. 7, a system model 714, corresponding to the system model of FIG. 5A, may receive control parameters 702, motor performance 704 (e.g., based on testing), thermal model 706 parameters such as drug temperatures, viscosity, etc. (e.g., based on testing and/or simulation), screw friction 708 (e.g., based on testing and/or simulation), plunger friction 710 (e.g., based on testing and/or simulation), fluid path resistance 712 (e.g., based on testing and/or simulation) and the like. The system model 714 may output performance metrics 716 (e.g., injection speed, motor stall margin, etc.), control scheme evaluations 718 (e.g., for the speed control loop output 510, current limit loop output 512, etc.), structural assembly outputs 720 (e.g., mechanical outputs including deformation, stiffness, strain), and plunger response outputs 722 (e.g., mechanical outputs including sealing pressure, glide force, deformation, stiffness, strain).

Figure 8A:
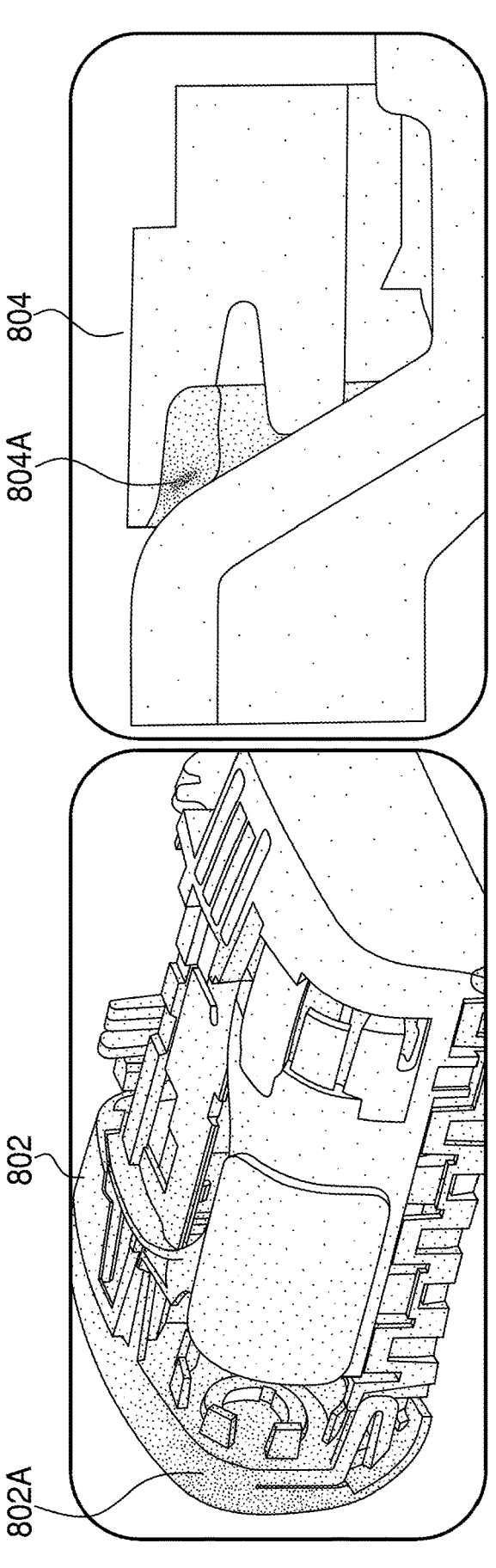
FIGS. 8A-8B show diagrams of structural assemblies, according to an example of the disclosure.
Figure 8B:
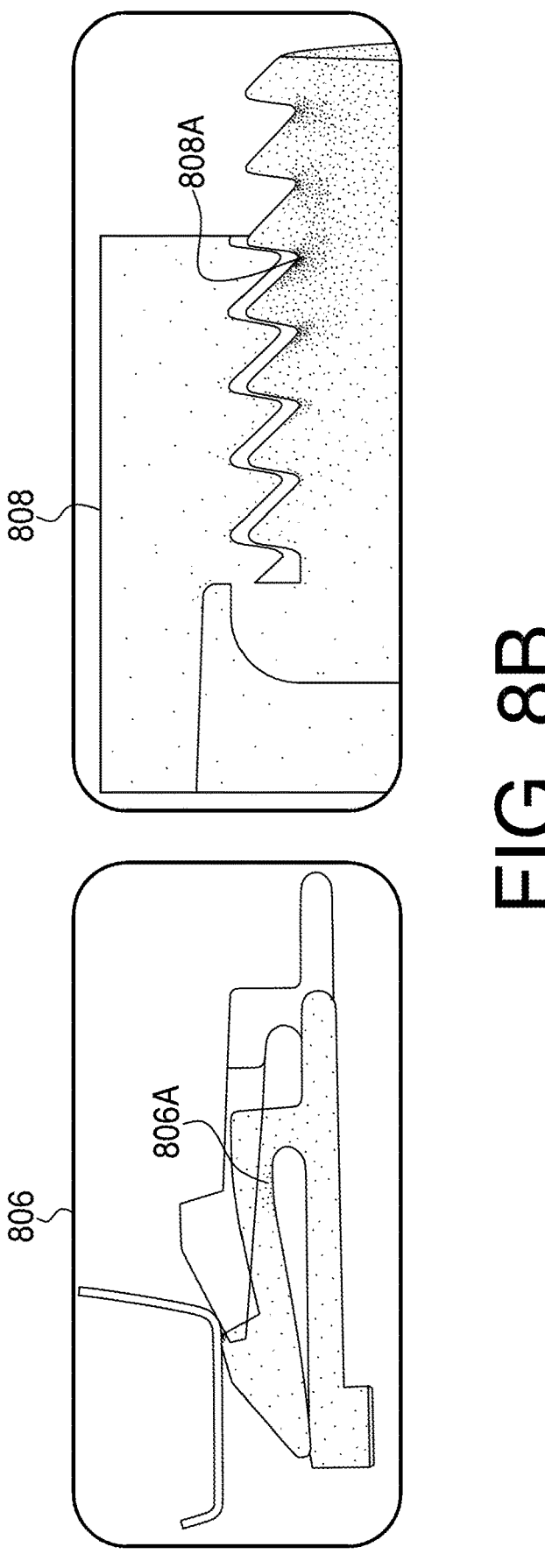

FIGS. 8A-8B show diagrams of simulated structural assemblies, in accordance with embodiments disclosed herein. Diagram 802, 804, 806, and 808 may be generated using a finite element method where the geometry of a given component (e.g., the auto-injector of diagram 802) is broken down into smaller sections and the stress and displacement fields are projected onto the component based on numerically determining the stress and displacement for each smaller section. Such components may be, but are not limited to, structural assemblies, snaps, screw threads, fluid paths (e.g., fluid path bends), or the like. Attributes (e.g., stress, displacement, etc.) of a given component may be based on elements such as plasticity, non-linear contact, hyper-elastic materials, etc. Diagram 802 shows an auto-injector with projected stress for each small section, where all of the small sections combined make up the auto-injector. The diagrams of FIGS. 8A-8B may be generated based on the outputs of the linear device model 402 of FIGS. 4 and 5A. For example, the diagram 802 of FIG. 8A shows the effect of the 200 N of maximum force value 602B.

As shown in FIG. 8A, the highest stress on the auto-injector of diagram 802 may be experienced at sections 802A that are shaded to indicate the higher stress. Similarly, the highest stress on the component of diagram 804 may be at sections 804A. The diagram 804 may be generated based on force applied when assembling the auto-injector of diagram 804 (e.g., based on connect a glass cartridge to a holder such that a force is generated when the two components are snapped together). Similarly, the highest stress on the component of diagram 806 may be at sections 806A. Diagram 806 may be generated based on a screw pushing on an auto-injector plunger. Similarly, the highest stress on the component of diagram 808 may be at sections 808A. The diagram 808 may be generated based on force applied when assembling the auto-injector of diagram 808 (e.g., in a manner similar to assembling the components of diagram 804).

Figure 9A:
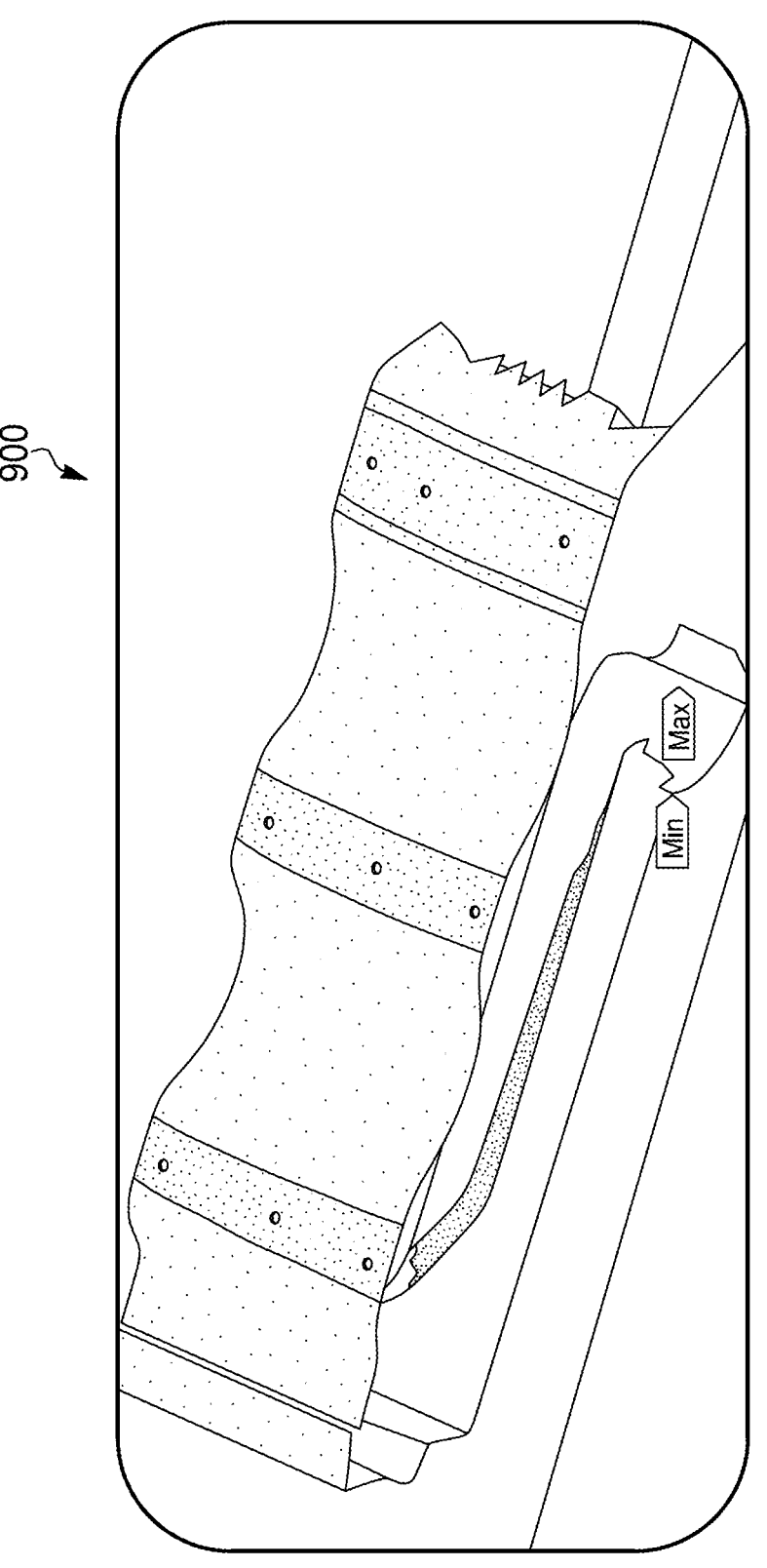
FIGS. 9A-9B show a plunger response, according to an example of the disclosure.
Figure 9B:
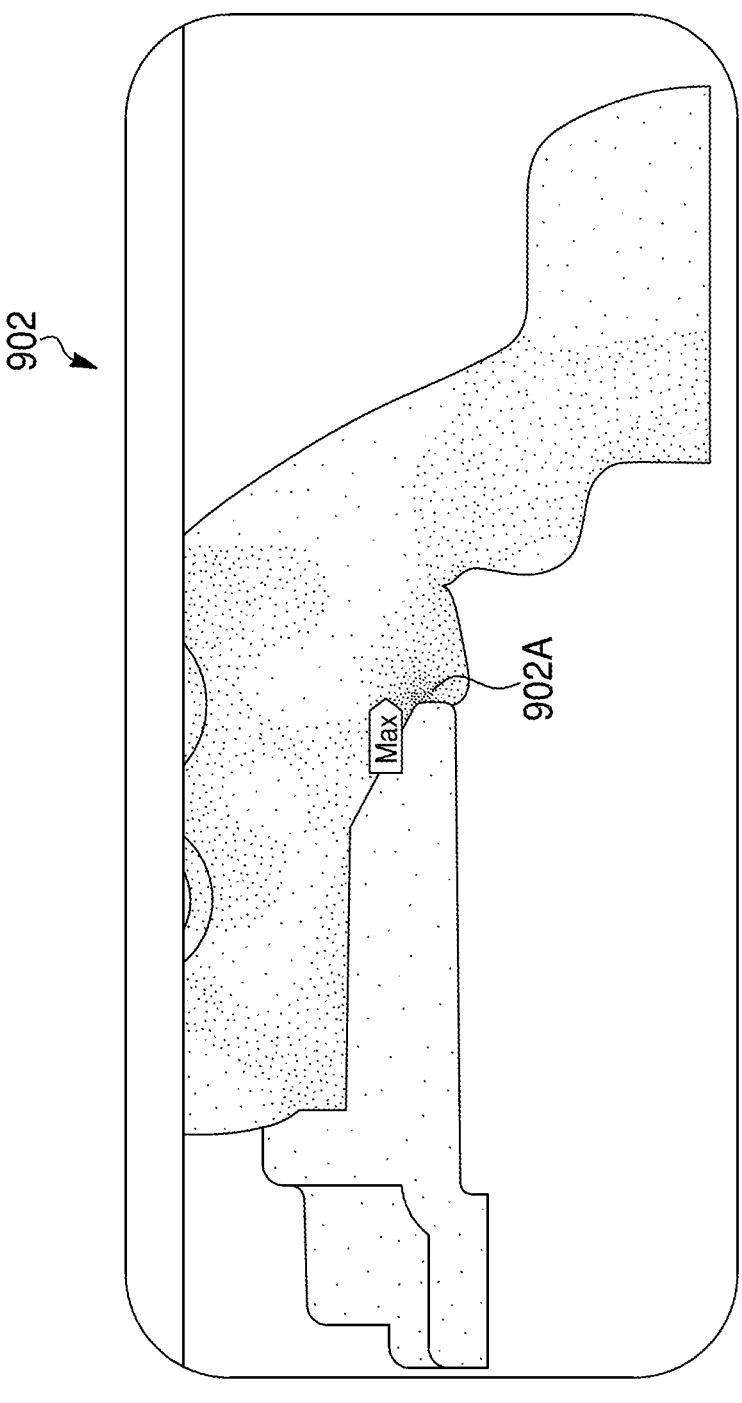

FIGS. 9A and 9B show diagrams of simulated structural assemblies, in accordance with embodiments disclosed herein. The diagrams shown in FIGS. 9A and 9B may be used to assess contact (e.g., sealing) pressure, characterize rod-plunger interaction, verify peak strain, predict drag force as a function of fluid pressure for a system model (e.g., amount of resistance against a glass), and/or the like. Diagram 900 may be generated using the finite element technique disclosed in reference to FIGS. 8A and 8B. Diagram 900 shows the sealing pressure of a rubber component on a glass component. If the sealing pressure is below a fluid pressure of a corresponding fluid, the fluid may leak as a result of the pressure difference. The 200 N of maximum force value 602B of FIG. 6 may be used to generate show the sealing pressure shown in diagram 900. Accordingly, a test may be implemented to determine if a leak may occur based on either a minimum force value 602A or the maximum force value 602B.

FIG. 9B includes a chart 902 showing the effect of pushing the plunger with 200 N of force (i.e., maximum force value 602B of FIG. 6). The force on the plunger may cause components to be pulled toward or pulled apart from each other. As shown in FIG. 9B, the 200 N of force may cause the component on the right to push towards the component on the left. The maximum force is indicated at 902A. A test may be implemented to determine if the push exceeds a threshold amount of push to maintain operation of the components shown in FIG. 9B.

Substance (e.g., drug) viscosity may be a function of substance temperature. According to an implementation of the disclosed subject matter, free and/or forced convection thermal analysis may be used to determine the behavior of substance temperature. For example, such thermal analysis may be used to determine the speed at which a substance changes temperature (e.g., when moved from a cold environment to a warm environment). Accordingly, the viscosity of a substance (e.g., a drug) may be estimated using a thermal analysis. The estimation may be based on the speed at which the substance changes temperatures when moved from a first environment to a second environment. The temperature of a medical device or component housing the substance and/or the transfer of the medical device, component, or substance from a first environment at a temperature to a second environment at a different temperature, may alter the viscosity of the substance. Such variance in viscosity may have device or component design implications. As examples, a relatively higher substance viscosity (e.g., as a result of relatively lower temperatures) may increase the mechanical load of a device or component, decrease the injection time of injection, change the probability of engaging a control loop (e.g., a higher viscosity may increase the probability of reaching a current limit), or the like.

Substance viscosity may be an input to a linear device model. Alternatively, one or more temperatures may be input into a linear device model which may determine substance viscosities based on the one or more temperatures. Output distributions output by a linear device model may be further based on substance viscosity and/or substance viscosity as a factor of time and/or temperature. For example, an output distribution for a device or component may be adjusted over a period of time based on the change in a substance viscosity over the period of time. The change in substance viscosity may be based on a change in temperature over that period of time (e.g., after removing a drug from a cold environment to a room temperature environment). The output distributions of a device or component may vary based on temperature and/or respective substance viscosity. For example, force output distribution 602 of FIG. 6 may be modified based on a range of potential temperatures and/or respective substance viscosities. The force output distribution 602 may, for example, have a higher and/or lower range or peak based on the temperatures and/or respective substance viscosities. Design of the device and/or component may be verified and/or rejected based on the modified force output distribution 602.

According to an implementation, a thermal analysis may be used to determine substance (e.g., drug) temperature behavior. The thermal analysis based temperature behavior may be used to estimate substance viscosity (e.g., over a period of time such as when the substance is moved from a first environment to a second environment with varying temperatures). A thermal analysis may include, for example, a free convection analysis, a forced convection analysis, or the like. FIG. 10 shows a free convection analysis 1010 corresponding to drug temperatures 1012 over time. Free convection analysis 1010 may be used to assess temperature transients during device warm-up (e.g., when moved from a refrigerated environment to room temperature). Drug temperatures 1012 identified based on the free convection analysis 1010, over a period of time, may inform drug viscosity. Free convection analysis 1010 may be based on an amount of ambient air circulation and the analysis shown via free convection analysis 1010 may provide greater understanding of sensitivities based on the ambient air circulation at or around a given device or component. Free convection analysis 1010 may be based on, at least in part, a simulation based on the flow of air generated based on temperature differences between a device or component and ambient conditions. Free convection analysis 1010 may be used when, for example, there is no external influence to move air beyond a temperature gradient introduced by a given device or component itself. According to the example shown in FIG. 10, drug temperatures 1012 may be input to a linear device model (e.g., linear device model 402). Alternatively or in addition, the drug temperatures 1012 may be provided as control loop output 510, as it may relate to the speed of a drug.

According to an implementation, sensed temperature values may be provided as an input to a device or component, or a controller used to control the same. The temperature values may be sensed using a temperature sensor that is internal or external to a given device or component. Sensed temperature values may be used to adjust control parameters for the device or component.

According to an implementation, coefficient C1 of FIG. 4 may be determined based on a combination of conditions such as the restriction amount of a needle that fluid is pushed through and/or a pitch of a leadscrew. FIG. 11 shows a fluid path restriction 1110 analysis to determine coefficient C1 based on the slope of the resulting chart 1112, based on the force exerted as a factor of viscosity and plunger velocity and/or flow rate. Fluid path restriction 1110 analysis may be used to predict plunger reaction force as a function of fluid viscosity and plunger travel speed, as shown in example chart 1112. Plunger force may be a function of needle geometry, drug viscosity, and/or plunger velocity. Fluid path restriction 1110 analysis may be a simulation based on a device or its components and may be a driver for device injection time.

The output distributions of a device or component may vary based on coefficient C1 determined based on fluid path restriction 1110 analysis. For example, force output distribution 602 of FIG. 6 may be modified based on the slope (C1) identified based on a device or component's simulated force as a factor of viscosity and speed. The force output distribution 602 may, for example, have a higher and/or lower range or peak based on the slope (C1). Design of the device and/or component may be verified and/or rejected based on the modified force output distribution 602.

FIG. 12 shows simulated drop testing results 1210, 1212, and 1214 as a factor of acceleration of time as shown in chart 1216. A drop testing simulation used to predict the drop testing results 1210, 1212, and 1214 may be used to predict acceleration and/or deformation of a given device or component over time. Such predictions may be used to extract forces between components, stresses in components, and/or strains of components. The force on a device or its components may be predicted using drop testing results 1210, 1212, and 1214. Drop testing results 1210, 1212, and 1214 may be generated for a collision based on accelerations over time, as shown in chart 1216. The device shown in drop testing results 1210, 1212, and 1214 may be approved or modified, based on the results.

FIG. 13A shows a component or device leakage assessment 1310, according to an implementation of the disclosed subject matter. For example, the leakage assessment may be for a Leur fitting used in a device or component. A leakage assessment may be performed to simulate potential leakage for a component or device. Such predictions may be based on performing an iterative analysis to determine if fluid pressure overcomes contact pressure between two or more surfaces. For example, fluid pressure penetration may be used to assess the risk of leakage in slip fittings designed for a component of design. The results of a leakage assessment may be used to modify attributes of fittings, such as slip fittings.

FIG. 13B shows component or device physiological modeling. A quantitative physiological model may be a mathematical representation that approximates the behavior of a physiological system (e.g., a body, body part, tissue 1314, etc.). A physiological model 1312 may describe a physiological system without the use of mathematics. The model may be applied to a dermis 1318, adipose layer 1316, and/or tissue 1314. Physiological model 1312 may be used to simulate the physiology of the body (e.g., of model tissue 1314) to predict its response to an injection of fluid.

FIG. 13C shows a needle coring simulation 1320. Needle coring simulation 1320 may be generated using an Arbitrary Lagrangian-Eulerian (ALE) technique and/or Smoothed Particle Galerkin (SPG) technique to refine needle tip geometries to, for example, reduce coring risk. Needle coring simulation 1320 may be used as a finite element model of needle coring using, for example, ALE and/or SPG techniques. As applied herein, needle coring may be when a needle removes material from a closure (e.g., as it pierces the closure). Such cores may be, for example, longitudinal in shape. Needle coring simulation 1320 may be used to simulate needle performance, to reduce coring in a designed needle used with a device or component. One or more simulations may be used to refine needle geometry and/or closure material selection.

FIG. 14 shows a product life cycle 1400 implemented for simulation driven development, in accordance with the techniques disclosed herein. Product life cycle 1400 may be used to generate better and/or fewer physical iterations of a device or product, can be used for focused design ideation, provides for virtual prototyping, increase design optimization, augment design characterization, support regulatory processes, improve root cause analysis, accelerate redesigns, and support changes.

As shown in FIG. 14, product life cycle 1400 may include discovery and ideation at 1402, which is followed by invention and prototyping 1404. Invention and prototyping 1404 may include iterations of design ideation 1406, virtual prototyping 1408, and design optimization 1411. Invention and prototyping 1404 may be implemented using the techniques disclosed herein. For example, linear device model 402 may be used for virtual prototyping 1408 and design optimization 1411. Pre-clinical testing may be conducted at 1412, followed by clinical testing at 1414. Regulatory decisions 1416 may be based on predicting success 1418 and/or predicting failures 1420. Product launch 1422 may be supplemented by post-market monitoring 1424. Post-market monitoring may include identifying root causes 1428 to facilitate redesigns 1426.

Any suitable system infrastructure may be put into place to generate the simulations and/or the data disclosed herein. Any of the disclosed systems or methods may be executed by or implemented by a computing system. Although not required, aspects of the present disclosure are described in the context of computer-executable instructions, such as routines executed by a data processing device, e.g., a server computer, wireless device, and/or personal computer. Those skilled in the relevant art will appreciate that aspects of the present disclosure can be practiced with other communications, data processing, or computer system configurations, including: Internet appliances, hand-held devices (including personal digital assistants ("PDAs")), wearable computers, all manner of cellular or mobile phones (including Voice over IP ("VoIP") phones), dumb terminals, media players, gaming devices, multi-processor systems, microprocessor-based or programmable consumer electronics, set-top boxes, network PCs, mini-computers, mainframe computers, and the like. Indeed, the terms "computer," "server," and the like, are generally used interchangeably herein, and refer to any of the above devices and systems, as well as any data processor.

Aspects of the present disclosure may be embodied in a special purpose computer and/or data processor that is specifically programmed, configured, and/or constructed to perform one or more of the computer-executable instructions explained in detail herein. While aspects of the present disclosure, such as certain functions, are described as being performed exclusively on a single device, the present disclosure may also be practiced in distributed environments where functions or modules are shared among disparate processing devices, which are linked through a communications network, such as a Local Area Network ("LAN"), Wide Area Network ("WAN"), and/or the Internet. In a distributed computing environment, program modules may be located in both local and remote memory storage devices.

Aspects of the present disclosure may be stored and/or distributed on non-transitory computer-readable media, including magnetically or optically readable computer discs, hard-wired or preprogrammed chips (e.g., EEPROM semiconductor chips), nanotechnology memory, biological memory, or other data storage media. Alternatively, computer implemented instructions, data structures, screen displays, and other data under aspects of the present disclosure may be distributed over the Internet and/or over other networks (including wireless networks), on a propagated signal on a propagation medium (e.g., an electromagnetic wave(s), a sound wave, etc.) over a period of time, and/or they may be provided on any analog or digital network (packet switched, circuit switched, or other scheme).

Features enumerated above have been described within the context of particular embodiments. However, as one of ordinary skill in the art would understand, features and aspects of each embodiment may be combined, added to other embodiments, subtracted from an embodiment, etc. in any manner suitable to assist with controlled preparation and/or delivery of a drug.

The following items are disclosed herein:

1. A method for determining accelerated testing parameters for a medical device, the method comprising:
   receiving raw creep modulus data relating creep strains to durations of stress and amounts of stress, as a factor of a range of temperatures;
   generating a predictive modulus based on the raw creep modulus data; and
   generating, using the predictive modulus, one or more of an accelerated testing time, an accelerated stress, or an accelerated temperature.
2. The method of item 1, wherein the accelerated testing time is generated based on a reference creep strain, a reference stress, and the accelerated temperature.
3. The method of item 2, further comprising:
   generating an accelerated testing creep strain based on accelerated testing of the medical device, the accelerated testing conducted based on the accelerated temperature, the accelerated testing time, and the accelerated stress; and outputting one of a medical device approval indication or a medical device rejection indication based on comparing the accelerated testing creep strain and the reference creep strain.

4. The method of item 3, wherein the approval indication approves the medical device and the rejection indication rejects the medical device.

5. The method of item 2, further comprising:

generating an accelerated testing creep strain based on accelerated testing of the medical device, the accelerated testing conducted based on the accelerated temperature, the accelerated testing time, and the accelerated stress; and outputting one of a predictive modulus approval indication or a predictive modulus rejection indication, based on comparing the accelerated testing creep strain and the reference creep strain.

6. The method of item 1, wherein the medical device is manufactured based on a medical device design corresponding to another medical device, wherein the raw creep modulus data is based on the other medical device.

7. The method of item 1, wherein the predictive modulus is generated based on a three-dimensional (3D) interpolation of the raw creep strain data.

8. The method of item 1, wherein the raw creep strain data is generated based on one of simulated strain or experienced strain.

9. A method for validating a predictive modulus for a medical device, the method comprising:

receiving raw creep strain data relating creep strain values to durations of stress and amounts of stress, as a factor of a range of temperatures;

generating a predictive modulus, the predictive modulus being configured to output an accelerated temperature, an accelerated time, and an accelerated stress based on a reference creep strain;

receiving the accelerated temperature, the accelerated time, and the accelerated stress based on the reference creep strain;

receiving an accelerated testing creep strain for the medical device based on accelerated testing conducted based on the accelerated temperature, the accelerated time, and the accelerated stress; and outputting one of an approval indication or a rejection indication based on comparing the accelerated testing creep strain and the reference creep strain.

10. The method of item 9, wherein the predictive modulus is generated based on a three-dimensional (3D) interpolation of the raw creep strain data.

11. The method of item 9, wherein a first creep strain for a first duration of time, a first amount of stress, and a first temperature is different than a second creep strain for the first duration of time, the first amount of stress, and a second temperature.

12. The method of item 9, wherein the reference creep strain corresponds to a reference temperature, a reference time, and a reference stress.

13. The method of item 12, wherein the reference temperature is an ambient temperature, the reference time is an anticipated shelf life for the medical device, and the reference stress is an anticipated amount of stress.

14. The method of item 9, wherein the approval indication approves the predictive modulus and the rejection indication rejects the predictive modulus.

15. A method for validating a medical device design, the method comprising:

receiving a plurality of medical device relationships based on the medical device design, wherein the plurality of medical device relationships correspond to voltage, current, resistance, torque, speed, and force relationships for the medical device design and comprise a plurality of coefficients;

generating a linear device model based on the plurality of medical device relationships;

receiving simulated coefficient values for each of the plurality of coefficients from a distribution function, for the plurality of medical device relationships;

generating simulated output distributions for a voltage, a current, a resistance, a torque, a speed, or a force, based on the simulated coefficients and the linear device model;

comparing the simulated output distributions to a threshold output requirement; and outputting one of an approval indication or a rejection indication based on comparing the simulated output distributions to the threshold output requirement.

16. The method of item 15, wherein the distribution function is a normal distribution function or a mixture of normal distribution functions.

17. The method of item 15, wherein comparing the simulated output distributions to the threshold output requirement comprises:

comparing a maximum distribution value to a maximum threshold output requirement, comparing a minimum distribution value to a minimum threshold output value, or comparing a peak distribution value to a peak threshold output value.

18. The method of item 15, wherein the simulated output distributions are based on at least ten thousand simulations performed in less than one hour.

19. The method of item 15, wherein the plurality of medical device relationships are based on a substance viscosity, wherein the substance viscosity is calculated based on a substance temperature behavior determined based on a thermal analysis.

20. The method of item 15, wherein a coefficient of the plurality of coefficients is generated based on a fluid path restriction analysis, the fluid path restriction analysis outputting a force exerted as a factor of determined viscosity and determined speed.

While a number of items are presented herein, multiple variations on such items, and combinations of elements from one or more items, are possible and are contemplated to be within the scope of the present disclosure. Moreover, those skilled in the art will appreciate that the conception upon which this disclosure is based may readily be used as a basis for designing other devices, methods, and systems for carrying out the several purposes of the present disclosure.

What is claimed is:

1. A method for determining accelerated testing parameters for a medical device, the method comprising:

receiving raw creep modulus data relating creep strains to durations of stress and amounts of stress for a first medical device, as a factor of a range of temperatures;

generating a predictive modulus for the first medical device based on the raw creep modulus data;

generating, using the predictive modulus, an accelerated testing time, an accelerated stress, or an accelerated temperature;

performing a first accelerated testing of a second medical device based on the accelerated testing time, the accelerated stress, or the accelerated temperature;

determining a first accelerated testing creep strain based on the first accelerated testing of the second medical device;

comparing an accelerated testing creep strain at a first target point of the first accelerated testing creep strain to a reference creep strain at a corresponding second target point of a reference creep strain associated with the first medical device, wherein the first target point is output by the predictive modulus; and outputting one of a second medical device approval indication or a second medical device rejection indication based on the first accelerated testing creep strain at the first target point not exceeding or exceeding the reference creep strain at the second target point by a threshold amount.

2. The method of claim 1, wherein the accelerated testing time is generated based on the reference creep strain, a reference stress, and the accelerated temperature.

3. The method of claim 1, wherein the second medical device approval indication approves the second medical device and the second medical device rejection indication rejects the second medical device.

4. The method of claim 2, further comprising:

generating a second accelerated testing creep strain based on a second accelerated testing of the first medical device, the second accelerated testing conducted based on the accelerated temperature, the accelerated testing time, and the accelerated stress; and outputting one of a predictive modulus approval indication or a predictive modulus rejection indication, based on comparing the second accelerated testing creep strain and the reference creep strain.

5. The method of claim 1, wherein the second medical device is manufactured based on a medical device design corresponding to the first medical device, wherein the raw creep modulus data is based on the first medical device.

6. The method of claim 1, wherein the predictive modulus is generated based on a three-dimensional (3D) interpolation of the raw creep modulus data.

7. The method of claim 1, wherein the raw creep modulus data is generated based on one of simulated strain or experienced strain.

8. A method for validating a predictive modulus for a medical device, the method comprising:

receiving raw creep strain data relating creep strain values to durations of stress and amounts of stress for a first medical device, as a factor of a range of temperatures;

generating a predictive modulus for the first medical device, the predictive modulus being configured to output an accelerated temperature, an accelerated time, and an accelerated stress based on a reference creep strain;

receiving the accelerated temperature, the accelerated time, and the accelerated stress based on the reference creep strain;

receiving an accelerated testing creep strain for the medical device based on accelerated testing conducted based on the accelerated temperature, the accelerated time, and the accelerated stress;

performing a first accelerated testing of the medical device based on the accelerated time, the accelerated stress, or the accelerated temperature;

determining a first accelerated testing creep strain based on the first accelerated testing of the medical device;

comparing an accelerated testing creep strain at a first target point of the first accelerated testing creep strain to a target reference creep strain at a corresponding second target point of the reference creep strain associated with the medical device; and outputting one of a predictive modulus approval indication or a predictive modulus rejection indication based on the first accelerated testing creep strain at the first target point not exceeding or exceeding the target reference creep strain at the second target point by a threshold amount.

9. The method of claim 8, wherein the predictive modulus is generated based on a three-dimensional (3D) interpolation of the raw creep strain data.

10. The method of claim 8, wherein a first creep strain for a first duration of time, a first amount of stress, and a first temperature is different than a second creep strain for the first duration of time, the first amount of stress, and a second temperature.

11. The method of claim 8, wherein the reference creep strain corresponds to a reference temperature, a reference time, and a reference stress.

12. The method of claim 11, wherein the reference temperature is an ambient temperature, the reference time is an anticipated shelf life for the medical device, and the reference stress is an anticipated amount of stress.

13. The method of claim 8, wherein the predictive modulus approval indication approves the predictive modulus and the predictive modulus rejection indication rejects the predictive modulus.

14. A system comprising:

an accelerated testing chamber configured to perform an accelerated testing;

a memory storing instructions; and a processor operatively connected to the memory and configured to execute instructions to perform operations comprising:

receiving raw creep modulus data relating creep strains to durations of stress and amounts of stress for a first medical device, as a factor of a range of temperatures;

generating a predictive modulus for the first medical device based on the raw creep modulus data; and generating, using the predictive modulus, an accelerated testing time, an accelerated stress, or an accelerated temperature;

performing, using the accelerated testing chamber, a first accelerated testing of a second medical device based on the accelerated testing time, the accelerated stress, or the accelerated temperature, wherein the processor is further configured to execute instructions to perform operations comprising:

receiving a first accelerated testing creep strain based on the first accelerated testing of the second medical device;

comparing an accelerated testing creep strain at a first target point of the first accelerated testing creep strain to a reference creep strain at a corresponding second target point of a reference creep strain associated with the first medical device, wherein the first target point is output by the predictive modulus; and outputting one of a second medical device approval indication or a second medical device rejection indication based on the first accelerated testing creep strain at the first target point not exceeding or exceeding the reference creep strain at the second target point by a threshold amount.

15. The system of claim 14, wherein the accelerated testing time is generated based on the reference creep strain, a reference stress, and the accelerated temperature.

16. The system of claim 14, wherein the second medical device approval indication approves the second medical device and the second medical device rejection indication rejects the second medical device.

17. The system of claim 14, wherein the second medical device is manufactured based on a medical device design corresponding to the first medical device, wherein the raw creep modulus data is based on the first medical device.

18. The system of claim 14, wherein the predictive modulus is generated based on a three-dimensional (3D) interpolation of the raw creep modulus data.

19. The system of claim 14, wherein the raw creep modulus data is generated based on one of simulated strain or experienced strain.

* * * * *